US006899868B2

(12) United States Patent
Messier

(10) Patent No.: US 6,899,868 B2
(45) Date of Patent: May 31, 2005

(54) IODINE/RESIN DISINFECTANT AND A PROCEDURE FOR THE PREPARATION THEREOF

(75) Inventor: Pierre Jean Messier, Quebec (CA)

(73) Assignee: Triosyn Holding Inc., Quebec (CA)

( * ) Notice: Subject to any disclaimer, the term of this patent is extended or adjusted under 35 U.S.C. 154(b) by 0 days.

(21) Appl. No.: 10/161,102

(22) Filed: May 31, 2002

(65) Prior Publication Data

US 2003/0099606 A1 May 29, 2003

Related U.S. Application Data

(63) Continuation of application No. 09/465,968, filed on Dec. 14, 1999, now abandoned, which is a division of application No. 08/803,869, filed on Feb. 24, 1997, now Pat. No. 6,045,820, which is a division of application No. 08/256,425, filed as application No. PCT/CA93/00378 on Sep. 15, 1993, now Pat. No. 5,639,452, which is a continuation-in-part of application No. 08/047,535, filed on Apr. 19, 1993, now abandoned, which is a continuation-in-part of application No. 07/957,307, filed on Sep. 16, 1992, now abandoned.

(51) Int. Cl.[7] ........................ A61K 31/74; A61K 31/785
(52) U.S. Cl. ................. 424/78.1; 424/78.11; 424/78.12
(58) Field of Search .......................... 424/78.1, 78.11, 424/78.12, 443, 76.8

(56) References Cited

U.S. PATENT DOCUMENTS

| 3,316,173 | A | 4/1967 | Mills |
| 3,462,363 | A | 8/1969 | Mills |
| 3,715,972 | A | 2/1973 | Kelsn |
| 3,817,860 | A | 6/1974 | Lambert |
| 3,923,665 | A | 12/1975 | Lambert |
| 4,076,622 | A | 2/1978 | Costin |
| 4,076,722 | A | 2/1978 | Fabian et al. |
| 4,113,851 | A | 9/1978 | Leveen |
| 4,187,183 | A | 2/1980 | Hatch |

(Continued)

FOREIGN PATENT DOCUMENTS

| BE | 853566 | 8/1977 |
| CA | 942188 | 12/1974 |
| CA | 1125651 | 6/1982 |
| DE | 196 49 237 A1 | 4/1998 |
| EP | 048286 | 3/1982 |
| EP | 0 347 746 A1 | 12/1989 |
| EP | 402865 | 12/1990 |

(Continued)

OTHER PUBLICATIONS

"Viricidal Capability of Resin–Triiodide Demand–Type Disinfectant"; Louis R. Final et al., *Applied and Environmental Microbiology*; Dec., 1982; pp. 1370–1373.

(Continued)

Primary Examiner—Thurman K. Page
Assistant Examiner—Blessing Fubara
(74) Attorney, Agent, or Firm—Goodwin Procter LLP

(57) ABSTRACT

The present invention relates to iodine demand disinfectants. It relates in particular to a process for preparing a polyiodide-resin for use as an iodine demand disinfectant wherein a porous strong base anion exchange resin in a salt form, is contacted with a material capable of donating a member absorbable by the resin so as to convert the resin to the polyiodide-resin. The adsorbable member is selected from the group comprising $I_2$ and polyiodide ion having a valence of −1. The process is characterized in that conversion of the anion exchange resin to the polyiodide-resin is effected at elevated temperature and elevated pressure, the elevated temperature being 100 degrees C. or higher, the elevated pressure being greater than atmospheric pressure. The present invention also relates to disinfectant substance comprising an iodine (impregnated) resin as produced by the above process.

12 Claims, 7 Drawing Sheets

U.S. PATENT DOCUMENTS

| | | | |
|---|---|---|---|
| 4,190,529 A | | 2/1980 | Hatch |
| 4,238,477 A | * | 12/1980 | Lambert et al. .............. 521/31 |
| 4,298,475 A | | 11/1981 | Gartner |
| 4,343,765 A | | 8/1982 | Elston |
| 4,381,380 A | | 4/1983 | LeVeen |
| 4,420,590 A | | 12/1983 | Gartner |
| 4,455,187 A | | 6/1984 | von Blücher |
| 4,469,826 A | | 9/1984 | Carlick |
| 4,483,771 A | | 11/1984 | Koch |
| 4,510,193 A | | 4/1985 | von Blücher |
| 4,526,751 A | | 7/1985 | Gartner |
| 4,749,484 A | | 6/1988 | Greenhut |
| 4,891,227 A | | 1/1990 | Thaman et al. |
| 4,925,517 A | | 5/1990 | Charbonneau et al. |
| 4,978,449 A | | 12/1990 | Devine |
| 4,983,192 A | | 1/1991 | von Blücher |
| 4,988,557 A | | 1/1991 | Charbonneau |
| 4,995,976 A | | 2/1991 | Vermes |
| 4,999,190 A | | 3/1991 | Final |
| 5,051,256 A | | 9/1991 | Barnes |
| 5,076,912 A | | 12/1991 | Belz |
| 5,110,479 A | | 5/1992 | Frommer et al. |
| 5,156,843 A | | 10/1992 | Leong |
| 5,176,836 A | | 1/1993 | Sauer |
| 5,277,963 A | | 1/1994 | von Blücher |
| 5,350,625 A | | 9/1994 | Peterson |
| 5,370,534 A | | 12/1994 | Wolf |
| 5,431,908 A | | 7/1995 | Lund |
| 5,433,987 A | | 7/1995 | Peterson |
| 5,614,301 A | | 3/1997 | Katz |
| 5,626,820 A | | 5/1997 | Kinkead |
| 5,639,452 A | | 6/1997 | Messier |
| 5,662,991 A | | 9/1997 | Smolik |
| 5,731,065 A | | 3/1998 | Stelzmüller |
| 5,769,992 A | | 6/1998 | Smolik |
| 5,772,738 A | | 6/1998 | Muraoka |
| 5,790,987 A | | 8/1998 | Sesselmann |
| 5,856,245 A | | 1/1999 | Caldwell et al. |
| 5,980,827 A | | 11/1999 | Messier |
| 6,045,820 A | * | 4/2000 | Messier ..................... 424/443 |
| 6,592,861 B2 | * | 7/2003 | Messier ..................... 424/78.1 |

FOREIGN PATENT DOCUMENTS

| | | |
|---|---|---|
| EP | 0 500 460 A1 | 8/1992 |
| EP | 0 592 001 A1 | 4/1994 |
| GB | 853566 | 11/1960 |
| GB | 2 252 047 A | 7/1992 |
| JP | 60-6730 | 1/1985 |
| JP | 60-243003 | 12/1985 |
| JP | 63-65923 | 3/1988 |
| WO | WO92/04921 | 4/1992 |
| WO | WO 94/01069 | 1/1994 |

OTHER PUBLICATIONS

International Search Report for PCT/CA93/00378, dated Jan. 14, 1994.

"Effect of Resin Disinfectants—I3 and I5 on Giardia Muris and Giardia Lamblia"; George L. Marchin et al., *Applied and Environmental Microbiology*; Nov., 1983; pp. 965–969.

"New Fibrous Ion Exchangers for Purification of Liquids and Gases"; Soldatov, V.S.; *Stu. Environ. Sci.*, 1984, vol. 23, pp. 353–364.

* cited by examiner

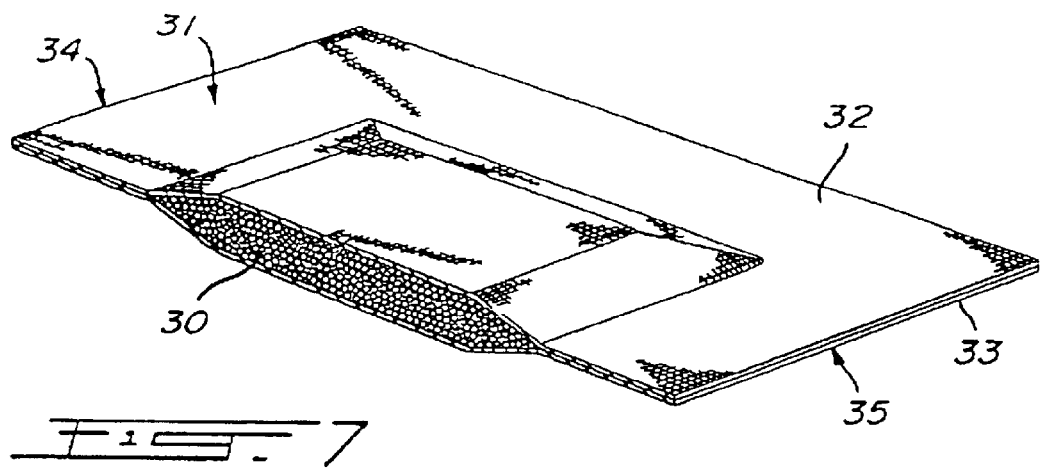
FIG. 7
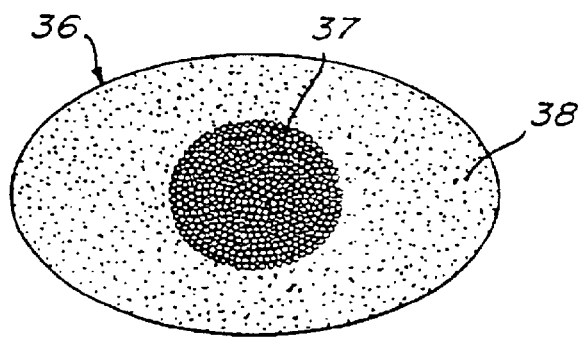
FIG. 8
FIG. 9
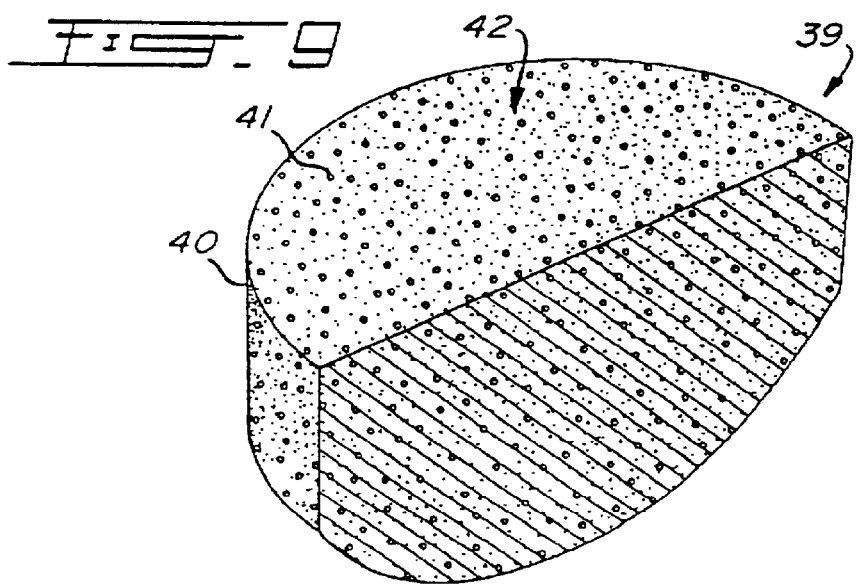

IODINE/RESIN DISINFECTANT AND A PROCEDURE FOR THE PREPARATION THEREOF

This is a continuation application of prior application U.S. Ser. No. 09/465,968, filed Dec. 14, 1999, now abandoned, which is a divisional of U.S. application Ser. No. 08/803,869, filed Feb. 24, 1997, now U.S. Pat. No. 6,045,820, which is a divisional application of U.S. application Ser. No. 08/256,425, filed Jul. 12, 1994, now U.S. Pat. No. 5,639,452, which is a Rule 371 of PCT Application Serial No. PCT/CA93/00378, filed Sep. 15, 1993, which is a continuation-in-part application of U.S. application Ser. No. 08/047,535, filed Apr. 19, 1993, now abandoned, which is a continuation-in-part application of U.S. application Ser. No. 07/957,307, filed Sep. 16, 1992, now abandoned.

The present application is a continuation-in-part of U.S. patent application Ser. No. 07/957,307 filed Sep. 16, 1992 and of U.S. patent application Ser. No. 08/047,535 filed on Apr. 19, 1993.

The present invention relates to a disinfectant substance comprising an iodine (impregnated) resin and to a process for the preparation thereof. The iodine/resin disinfectant may be used to sterilize a fluid such as, for example, water, air, as well as fluid exudate secreted at body lesions or traumas such as at cuts, burns, etc.; thus, the disinfectant may be used to devitalize microorganisms (e.g. bacteria, viruses, etc . . . ) which may be present in the fluid (e.g. water, air, pus and the like). The treatment of fluid, such as water or air, with an iodine/resin disinfectant of the present invention may leave behind non-detectable (or acceptable) residual diatomic iodine in the fluid (e.g. water or air). The present invention in particular relates to a demand type broad spectrum resin-polyiodide (e.g. water, air, wound) disinfectant.

Diatomic halogen (such as $I_2$, $Cl_2$, $Br_2$, etc . . . ) has traditionally been used to disinfect water. Diatomic chlorine, for example, is a widely exploited disinfectant for controlling or eliminating micro-organisms which may be present in water. A disadvantage of a sterilization regime which exploits diatomic halogen is that the regime may leave behind unacceptable (residual) levels of halogen in the water once sterilization is complete.

An iodine/resin product has, however, been proposed for use as a demand disinfectant, namely a disinfectant wherein iodine is released almost entirely on a demand-action basis. U.S. Pat. Nos. 3,817,860, 3,923,665, 4,238,477 and 4,420,590 teach such a demand disinfectant wherein iodine is the active disinfectant agent; the entire contents of each of these patents is incorporated herein by reference. In accordance with the teachings of these patents the resin product may be used without fear of introducing unacceptable concentrations of diatomic iodine into the water to be sterilized.

U.S. Pat. Nos. 3,817,860 and 3,923,665 teach an iodine/resin demand disinfectant which is the reaction product obtained by contacting a strong base anion exchange resin with a suitable source of triiodide ions. The reaction product is taught as being very stable in the sense that the amount of iodine (e.g. $I_2$) released into water from the reaction product is sufficiently low that the water disinfected thereby is immediately ready for use, ie. as drinking water.

In accordance with the teachings of U.S. Pat. Nos. 3,817,860 and 3,923,665 the procedure for preparing the iodine/resin comprises forming a triiodide ion (solution or sludge) by dissolving diatomic iodine in a water solution of a suitable alkali metal halide (e.g. KI, NaI, . . . ). The triiodide solution is in particular taught as being made with a minimal (i.e. minor) water content just sufficient to avoid causing the $I_2$ to crystallize out; see example 1 of U.S. Pat. No. 3,923,665. The resulting (solution) containing the triiodide ion is then contacted with the starting resin (under ambient conditions with respect to temperature (i.e. 25 to 30° C.) and pressure), the triiodide ions exchanging with the anion of the resin (e.g. exchange with chlorine, sulfate, etc., . . . ). The starting resin is taught as being a porous granular strong base anion exchange resin having strongly basic groups in a salt form wherein the anion thereof is exchangeable with triiodide ions. In accordance with the teachings of the above prior art references contacting is continued until the desired amount of triiodide has reacted with the strongly basic groups such that bacterially contaminated water is disinfected when passed through a bed of the obtained resin. After a suitable contact time the iodine/resin is (water) washed to remove water-elutable iodine from the resin product.

However, as indicated in U.S. Pat. No. 4,238,477, it is difficult to use the procedures outlined in the two previously mentioned U.S. patents so as to obtain a homogeneous iodine/resin product containing only triiodide anions and wherein all of the active sites of the resin have been converted to triiodide ions.

Accordingly, U.S. Pat. No. 4,238,477 teaches an alternate process whereby the iodine/resin may be produced. In accordance with this alternate impregnation/contact process, a suitable resin in the iodide form ($I^-$) is contacted with water comprising diatomic iodine ($I_2$) in solution, the water being recycled between a source of a predetermined amount of diatomic iodine and the resin. The process as taught by this latter patent, however, is a relatively complicated system of pumps, vessels, heaters, etc.; by exploiting a fluidized bed, it in particular may lead to a significant degree of resin bead attrition, i.e. particle breakup.

The processes as taught in U.S. Pat. Nos. 3,817,860 and 3,923,665 are carried out at ambient temperature and ambient pressure conditions. The U.S. Pat. No. 4,238,477 teaches that the contact may occur at a higher temperature such as 60 to 95° C. but that the temperature must be a non-boiling temperature (with respect to water); see column 3 lines 55 to 66.

The above referred to U.S. patents teach the use of the demand disinfectant iodinated resins for treating water; see also U.S. Pat. Nos. 4,298,475 and 4,995,976 which teach water purification devices or systems which exploit iodinated resins. None of these patents teaches the use of the iodinated resins for the purpose of sterilizing air.

It is also known to use iodine tincture for sterilising wounds. The sterilisation effect of iodine tincture is short lived; this means that the tincture must be reapplied on a regular basis to maintain the sterilisation effect. However, such solutions may also damage or destroy the tissue around the wound if applied too liberally and too often. Additionally, the direct application of such solutions to a lesion or wound is usually accompanied by a painful sensation.

Accordingly it would be advantageous to have a iodine/resin product which has improved characteristics over known or commercially available iodine/resin disinfectant products.

It would also be advantageous to have an alternate process for the preparation of a iodine/resin product (which has improved characteristics over the previously known iodine/resin).

It would be advantageous to have an alternative effective demand disinfectant (e.g. bactericidal) resin and an effective technique for the manufacture thereof. It would, in particular, be advantageous to have an iodine/resin demand disinfectant having a relatively low level of iodine bleed into a fluid (such as water or air) being treated as well as an iodine impregnation process for obtaining such iodinated resin.

It would also be advantageous to have a means whereby lesions, such as for example wounds or burns, may be treated in order to facilitate healing by devitalising microorganisms which may already be in the area of the lesion and further to prevent microorganisms from having access to such lesion (i.e. a dressing), i.e. to inhibit access from any outside biovectors such as for example airborne, waterborne, spital borne, blood borne, particulate borne microorganisms and the like.

It would additionally be advantageous to have a means for inhibiting or preventing microorganisms from contacting predetermined areas of the body such as the skin (e.g. a protective textile for making protective clothing).

In accordance with a general aspect, the present invention provides a process for preparing a demand disinfectant resin, said disinfectant resin being an iodinated strong base anion exchange resin, (i.e. a demand disinfectant-resin comprising polyiodide ions, having a valence of −1, the ions being absorbed or impregnated into the resin as herein described), the process comprising a conversion step, the conversion step comprising contacting a porous strong base anion exchange resin in a salt form with a sufficient amount of an iodine-substance absorbable by the anion exchange resin such that the anion exchange resin absorbs said iodine-substance so as to convert the anion exchange resin to the disinfectant-resin, said iodine-substance being selected from the group comprising $I_2$ (i.e. diatomic iodine) and polyiodide ions having a valence of −1, characterized in that for the conversion step at least a portion of the absorption of iodine-substance is effected at elevated temperature and at elevated pressure, said elevated temperature being 100° C. or higher (e.g. a temperature higher than 100° C. such as, for example, 102° C., 103° C., 104° C., 105° C., 110° C., 115° C., 150° C., etc.), said elevated pressure being greater than atmospheric pressure (e.g. a pressure greater than barometric pressure such as for example 2 psig, 3 psig, 4 psig, 5 psig, 15 psig, 25 psig, 35 psig, 100 psig, etc.).

In accordance with the present invention the disinfectant-resin may be one in which diatomic iodine is incorporated. The disinfectant polyiodide-resin may in particular be triiodide-resin. Thus, for example, the iodine-substance may comprise triiodide ion of formula $I_3^-$, i.e. so as to form a disinfectant-resin which comprises (absorbed) triiodide ions of formula $I_3^-$.

The terms "triiodide", "triiodide ion" and the like, as used in the context herein, refer to or characterize a substance or a complex as containing three iodine atoms and which has a valence of −1. The triiodide ion herein therefore is a complex ion which may be considered as comprising molecular iodine (i.e. iodine as $I_2$) and an iodine ion (i.e. $I^-$). Similarly the terms "polyiodide". "polyiodide ions" and the like, refer to or characterize a substance or a complex as having three or more iodine atoms and which may be formed if more of the molecular iodine combines with the monovalent triiodide ion. These terms are more particularly described in the above referred to U.S. patents.

In accordance with a further aspect, the present invention provides a process for preparing a demand disinfectant resin, said disinfectant resin being an iodinated strong base anion exchange resin, (i.e. a demand disinfectant-resin comprising polyiodide ions, having a valence of −1, the ions being absorbed or impregnated into the resin as herein described), the process comprising a conversion step, the conversion step comprising contacting a porous strong base anion exchange resin in a salt form other than the iodide form $I^-$, with a sufficient amount of an iodine-substance absorbable by the anion exchange resin such that the anion exchange resin absorbs said iodine-substance so as to convert the anion exchange resin to the disinfectant-resin, said iodine-substance being selected from the group comprising polyiodide ions having a valence of −1, characterized in that for the conversion step at least a portion of the absorption of iodine-substance is effected at elevated temperature and at elevated pressure, said elevated temperature being 100° C. or higher (e.g. a temperature higher than 100° C.), said elevated pressure being greater than atmospheric pressure (e.g. a pressure greater than barometric pressure).

The strong base anion exchange resin may be in a salt form such as for example a chloride or hydroxyl form.

The conversion in accordance with the present invention may essentially or at least partially be effected at said elevated temperature and elevated pressure. The conversion, in accordance with the present invention, may, thus for example, be effected in one, two or more stages. For example, the elevated pressure/temperature conditions may be divided between two different pairs of elevated pressure/temperature conditions, e.g. an initial pressure of 15 psig and a temperature of 121° C. and a subsequent pressure of 5 psig and a temperature of 115° C.

If the conversion is to be carried out in two stages, it may for example, comprise a first stage followed by a second stage. The first stage may, for example, be effected at low temperature conditions (e.g. at ambient temperature and ambient pressure conditions) whereas the second stage may be effected at elevated conditions such as described herein.

Thus, the present invention, in accordance with another aspect provides a process for preparing a demand disinfectant resin, said disinfectant resin being an iodinated strong base anion exchange resin, (i.e. a demand disinfectant-resin comprising polyiodide ions, having a valence of −1, the ions being absorbed or impregnated into the resin as herein described), the process comprising a conversion step, the conversion step comprising contacting a porous strong base anion exchange resin in a salt form with a sufficient amount of an iodine-substance absorbable by the anion exchange resin such that the anion exchange resin absorbs said iodine-substance so as to convert the anion exchange resin to the demand disinfectant resin, said iodine-substance being selected from the group comprising $I_2$ and polyiodide ions having a valence of −1, characterized in that said conversion step comprises an initial conversion stage followed by a second conversion stage, in that said initial conversion stage comprises contacting the anion exchange resin with the iodine-substance at a temperature of 100° C. or lower so as to obtain an intermediate composition, said intermediate composition comprising residual absorbable iodine-substance and an intermediate iodinated resin, (i.e. a resin comprising absorbed polyiodide ions having a valence of −1), and in that said second conversion stage comprises subjecting the intermediate composition to elevated temperature and elevated pressure, said elevated temperature being 100° C. or higher (e.g. a temperature higher than 100° C.), said elevated pressure being greater than atmospheric pressure.

In accordance with a further particular aspect, the present invention provides a process for preparing a demand disinfectant resin, said disinfectant resin being an iodinated strong base anion exchange resin, (i.e. a demand disinfectant-resin comprising polyiodide ions, having a valence of −1, the ions being absorbed or impregnated into the resin as herein described), the process comprising a conversion step, the conversion step comprising contacting a porous strong base anion exchange resin in a salt form other than the iodide form I⁻ with a sufficient amount of an iodine-substance absorbable by the anion exchange resin such that the anion exchange resin absorbs said iodine-substance so as to convert the anion exchange resin to the disinfectant-resin, said iodine-substance being selected from the group comprising polyiodide ions having a valence of −1, characterized
in that said conversion step comprises an initial conversion stage followed by a second conversion stage,
in that said initial conversion stage comprises contacting the anion exchange resin with the iodine-substance at a temperature of 100° C. or lower so as to obtain an intermediate composition, said intermediate composition comprising residual absorbable iodine-substance and an intermediate iodinated resin (i.e. a resin comprising absorbed polyiodide ions having a valence of −1),
and
in that said second conversion stage comprises subjecting the intermediate composition to elevated temperature and elevated pressure, said elevated temperature being 100° C. or higher (e.g. a temperature higher than 100° C.), said elevated pressure being greater than atmospheric pressure.

In accordance with the present invention, for the first stage, the low temperature may, for example, be a non-boiling temperature of not more than 95° C.; e.g. 15 to 60° C.; e.g. ambient temperature or room temperature such as a temperature of from about 15° C. to about 40° C., e.g. 20 to 30° C. The pressure associated with the low temperature condition of the first stage may, for example, be a pressure of from 0 (zero) to less than 2 psig; the pressure may in particular be essentially ambient pressure (i.e. a pressure of less than 1 psig to 0 (zero) psig; 0 psig reflecting barometric or atmospheric pressure).

In accordance with the present invention, for the second stage, the elevated temperature may, for example, be: a temperature of 102° C. or higher; e.g. 105° C. or higher; e.g. 110° C. or higher; e.g. 115° C. or higher; e.g. up to 150° C. to 210° C.; e.g. 115° C. to 135° C. The elevated pressure associated with the elevated temperature condition of the second stage may, for example, be: a pressure of 2 psig or greater; e.g. 5 psig or greater; e.g. 15 psig to 35 psig; e.g. up to 100 psig.

The present invention further relates to any demand disinfectant resin, the disinfectant resin being an iodinated strong base anion exchange resin which is the same as an iodinated strong base anion exchange resin prepared in accordance with a process as defined herein; an iodinated resin the same as a resin prepared in accordance with the (particular) process described herein is one which has the same low iodine bleed characteristic, i.e. the iodine is (more) tenaciously associated with the resin than for previously known iodinated resins. It in particular relates to a demand disinfectant resin, the disinfectant resin being an iodinated strong base anion exchange resin whenever prepared in accordance with a process as defined herein.

The present invention also relates to the use of iodinated resins to disinfect fluids containing microorganisms, such fluids including air, water, pus, and the like. The iodinated resin may for example be a known resin such as discussed herein, a resin in accordance with the present invention, nylon based resin beads impregnated with iodine (such as MCV resin from MCV Tech. Intn'l Inc.), and the like.

Thus the present invention also provides a method for disinfecting air containing airborne microorganisms, said method comprising passing said air over a disinfectant resin such that airborne microorganisms contact said resin and are devitalized thereby, said disinfectant resin comprising an iodinated resin. The disinfectant resin may, for example, be a demand disinfectant resin. The disinfectant resin may, for example, comprise an iodinated strong base anion exchange resin.

The present invention further provides a system for disinfecting air containing airborne microorganisms, said system comprising
  means for providing an air path for the movement of air therethrough,
and
  a disinfectant resin disposed in said air path such that airborne microorganisms in air passing through said air path are able to be brought into contact with said resin and be devitalized thereby,
said disinfectant resin comprising an iodinated resin. The disinfectant resin may, for example, be a demand disinfectant resin. The disinfectant resin may, for example, comprise an iodinated strong base anion exchange resin.

The present invention additionally provides a combination comprising
  a disinfectant component
and
  a carrier component,
said disinfectant component comprising particles of an iodinated resin,
said particles of said disinfectant component being held (e.g. fixed) to said carrier component. The disinfectant component may, for example, be a demand disinfectant component. The disinfectant resin may, for example, comprise an iodinated strong base anion exchange resin. The combination may be used as a means for providing a barrier or shield for the body against microorganisms. The combination may thus, for example, be incorporated into a textile or other wearing apparel starting material in the form of a layer (e.g. a liner layer). The obtained raw wearing apparel material may then be used to make a protective garment, glove, sock, footwear (e.g. shoe), helmet, face mask and the like; the obtained wearing apparel may be worn in hazardous environments to protect the wearer from contact with viable microorganisms. The combination as desired or as necessary may flexible or stiff; depending on the nature of the carrier component and also on the form of the resin (e.g. plate, particle, etc.).

The present invention in a more particular aspect provides a sterilisation dressing, for being applied to a lesion, (such as a sore, a wound (e.g. cut), an ulcer, a boil, an abrasion, a burn or other lesion of the skin or internal organ), said dressing comprising
  a disinfectant component
and
  a carrier component,
said disinfectant component comprising particles of an iodinated strong base anion exchange resin, said carrier component being configured so as to hold onto particles of said disinfectant component such that microorganisms are able to be brought into contact with said particles and be devitalised thereby, said carrier component being of a pharmaceutically acceptable material. The disinfectant component may, for example, be a demand disinfectant. The disinfectant resin may, for example, comprise an iodinated strong base anion exchange resin. The carrier component may be stiff or it may be flexible as desired. The (sterilization) dressing may, for example, be applied over a wound or burn and be held in place over the time period needed for the body to repair the damaged area; the dressing during this time will act not only as a barrier or shield to prevent infectious microorganisms from contacting the lesion but also to sterilize the immediate area around the lesion including sterilising any fluid exudate such as pus which may exude from the lesion. Surprisingly, it has, for example, been found that even with relatively prolonged exposure of (guinea pig) skin to the active element of the dressing (i.e. the demand disinfectant) no irritation or inflammation was noted. It has also surprisingly been found that the dressing may effect infectious agents deep beneath the skin or dressing. The healing process may thus be hastened by the application of a (sterilization) dressing in accordance with the present invention.

The demand disinfectant for the above mentioned method and system for treating air as well as for the combination and the dressing may be an iodinated resin produced in accordance with the present invention or it may be a known demand disinfectant iodinated resin such as for example as mentioned herein.

The demand disinfectant depending on the intended use may take on any desired form; it may be bulk form; it may be in sheet form; it may be in particulate or granular form (e.g. particles of resin of from 0.2 mm to 1 cm in size), etc. . . .

It is to be understood herein, that if a "range" or "group of substances" is mentioned with respect to a particular characteristic (e.g. temperature, presssure, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a pressure greater than atmospheric, this is to be understood as specifically incorporating herein each and every individual pressure state, as well as sub-range, above atmospheric, such as for example 2 psig, 5 psig, 20 psig, 35.5 psig, 5 to 8 psig, 5 to 35, psig 10 to 25 psig, 20 to 40 psig, 35 to 50 psig, 2 to 100 psig, etc . . . ;

with respect to a temperature greater than 100° C., this is to be understood as specifically incorporating herein each and every individual temperature state, as well as sub-range, above 100° C., such as for example 101° C., 105° C. and up, 110° C. and up, 115° C. and up, 110 to 135° C., 115° C. to 135° C., 102° C. to 150° C., up to 210° C., etc.;

with respect to a temperature lower than 100° C., this is to be understood as specifically incorporating herein each and every individual temperature state, as well as sub-range, below 100° C., such as for example 15° C. and up, 15° C. to 40° C., 65° C. to 95° C., 95° C. and lower, etc.;

with respect to residence or reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

and similarly with respect to other parameters such as low pressures, concentrations, elements, etc. . . .

It is also to be understood herein that "g" or "gm" is a reference to the gram weight unit; that "C" is a reference to the celsius temperature unit; and "psig" is a reference to "pounds per square inch guage".

In drawings which illustrate example embodiments of the present invention:

FIG. 7 is a partially cut away perspective view of a sterilisation dressing of tea-bag type construction wherein the iodinated resin particles are free flowing but are held together by being enveloped by a fluid (e.g. air-liquid) permeable envelope of paper, gauze, plastics material, etc.;

FIG. 8 is a perspective view of a band-aid type sterlization dressing, wherein the iodinated resin particles are fixed to a central portion of an outer surface of a flexible band-aid carrier;

FIG. 9 is a perspective partially cut away view of a sterilisation foam or sponge type dressing comprising a flexible foam matrix having iodinated resin particles dispersed therein, the foam matrix having a relatively small pore size structure;

Figure 10:
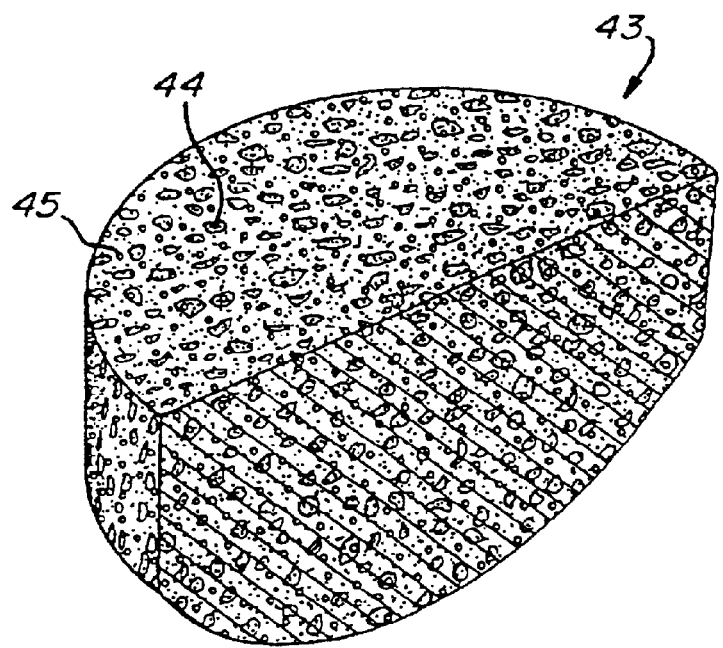
Figure 11:
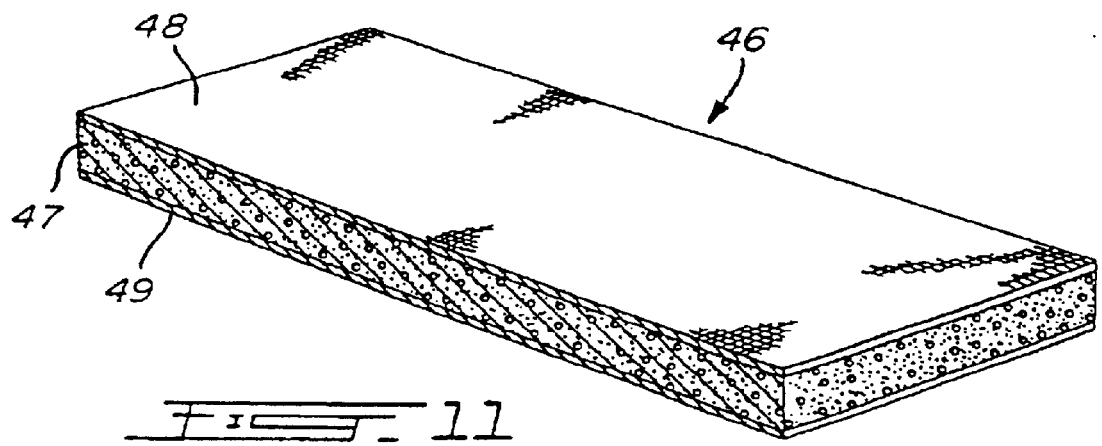

FIG. 10 is a perspective partially cut away view of a sterilisation foam or sponge type dressing comprising a flexible foam matrix having iodinated resin particles dispersed therein, the foam matrix having a relatively large pore size structure; and FIG. 11 is a cross sectional view of a sandwich type of textile material for use in the preparation of protective clothing, the textile including a layer of a flexible foam matrix such as is shown in FIG. 10.

In accordance with the present invention, the elevated temperature may as mentioned above, for example, be in the range of from 105° C. to 150° C.; the elevated pressure may be 5 psig and up.

In accordance with the process of the present invention the anion exchange resin may, for example, as described below, be a quaternary ammonium anion exchange resin; the anion exchange resin may be in the chloride form $Cl^-$, in the hydroxyl form $OH^-$; etc. . . .

In accordance with the present invention the obtained iodide-resin may be treated prior to use to remove any water-elutable iodine from the iodide-resin. The treatment (e.g. washing) may be continued until no detectable iodine is found in wash water (the wash water initially being ion free water). Any suitable (known) iodine test procedure may be used for iodine detection purposes (see for example the above mentioned U.S. patents.

In accordance with the present invention, the absorbable iodine substance may, for example, be provided by a composition consisting of mixture of KI, $I_2$ and a minor amount of water, the mole ratio of KI to $I_2$ initially being about 1; the expression "minor amount of water" as used herein shall be understood as characterizing the amount of water as being sufficient to avoid $I_2$ crystallization.

The present invention in a further aspect provides an enhanced iodine/resin demand disinfectant product in which more iodine may be distributed throughout and be more tenaciously associated with the resin (e.g. beads) than with the previously known or commercially available techniques, the disinfectant being produced by a process as described herein. The invention more particularly provides an enhanced triiodide-resin disinfectant.

The present invention can be practised with any (known) strong base anion exchange resin (for example, with those such as are described in more detail in the above-mentioned U.S. patents such as U.S. Pat. No. 3,923,665). A quaternary ammonium anion exchange resin is, however, preferred. As used herein, it is to be understood that the expression "strong base anion exchange resin" designates a class of resins which either contain strongly basic "cationic" groups, such as quaternary ammonium groups or which have strongly basic properties which are substantially equivalent to quaternary ammonium exchange resins. U.S. Pat. Nos. 3,923,665 and 3,817,860 identify a number of commercially available quaternary ammonium resins, as well as other strong base resins including tertiary sulphonium resins, quaternary phosphonium resins, alkyl pyridinium resins and the like.

Commercially available quaternary ammonium anion exchange resins which can be used in accordance with the present invention include in particular, Amberlite IRA-401 S, Amberlite IR-400 ($Cl^-$), Amberlite IR-400 ($OH^-$), Amberlite IR-402 ($Cl^-$), etc., (from Rohm & Hass) which may be obtained in granular form. These resins may for example, contain quaternary ammonium exchange groups which are bonded to styrene-divinyl benzene polymer chains.

The resins which may be used herein may be in a hydroxyl form, a chloride form or in another salt (e.g. sulphate) form provided that the anion is exchangeable with the iodine member (e.g. with triiodide ion).

The starting resin may, for example, be granular (i.e. comprise a plurality of particles) such that the final product will likewise have a granular or particulate character; the granular form is advantageous due to the high surface area provided for contact with microorganisms. The starting resin may, for example, comprise granules having a size in the range of from 0.2 mm to 0.8 cm (e.g. of from 0.35 mm to 56 mm).

Commercially available resins such as those mentioned above are available in the salt form (e.g. as the chloride) and in the form of porous granular beads of various mesh sizes; the resin may of course be used in a bulk or massive form such as a plate, sheet, etc. . . .

In accordance with the present invention, for example, a resin may be converted from a non-iodide form (e.g. a chloride form, a sulphate form) to the $I_3^-$ form. Suitable halide salts include alkali metal halides (such as KI, NaI, . . . ); potassium iodide is preferred. Alternatively, an iodide form of the resin may be used and the resin contacted with a source of diatomic iodine.

In accordance with the present invention any material or substance capable of donating an iodine-member absorbable by the anion exchange resin so as to convert the anion exchange resin to the desired polyiodide-resin may be used, as long as the denotable iodine-member thereof is a polyiodide ion having a valence of −1 and/or diatomic iodine. Examples of such materials in relation to iodine are shown in the above mentioned U.S. patents; e.g. compositions comprising iodine ($I_2$) and alkali metal halide (KI, NaI, etc. . . . , KI being preferred) in association with water. Alternatively, if the resin is in an iodide salt form ($I^{-1}$) the material may comprise the corresponding iodine in gaseous form.

Thus, for example, if a triiodide-resin is desired the resin may be contacted with an alkali metal iodide/$I_2$ mix wherein the iodide and the diatomic iodine are present in more or less stoichiometric amounts (i.e. a mole ratio of 1); see the previously mentioned U.S. patents. By applying stoichiometric amounts of the iodine ion and iodine molecule (i.e. one mole of $I_2$ per mole of $I^{-1}$), the iodide sludge will comprise substantially only the triiodide ions. If stoichiometric excess quantities of $I_2$ are used some of the higher polyiodide ions may be formed. Preferably, no more than the stoichiometric proportions of $I^-$ and $I_2$ are used in the initial aqueous starting sludge so that substantially only triiodided attaches to the resin.

For example iodine may be combined with sodium, potassium or ammonium iodide and some water. The composition will contain monovalent iodine ion which will combine with diatomic iodine ($I_2$) to form polyiodide ion. The molar ratio of iodine ion to diatomic iodine will dictate the nature of the polyiodide ion present, i.e. triiodide ion, mixtures of triiodide ion and other higher polyiodides ions, pentaiodide ion, etc. . . . Using about 1 mole of iodine ion per mole of diatomic iodine the formation of triiodide ion will be favoured. If stiochiometric excess of diatomic iodine is used this will favour the formation of higher polyiodides.

The determination of the (total) amount of iodine to be contacted with the resin, residence times etc. . . . , will depend upon such factors as the nature of the polyiodide it is desired to introduce into the structure of a resin; the nature of the starting resin (i.e. porosity, grain size, equivalent exchange capacity of the resin, etc.), etc. . . . Thus, for example, to determine the amount of iodine required to prepare a polyiodide resin, the equivalent exchange capacity of the resin needs to be known. If necessary, this can be readily determined for example by the procedure described in U.S. Pat. No. 3,817,860 (column 9, lines 15 to 28). The components of the process may be chosen such that the obtained iodinated strong base anion exchange resin may comprise a strong base anion exchange resin component which represents from 25 to 90 (preferably 45 to 65) percent by weight of the total weight of the obtained iodinated resin.

The conversion at elevated conditions, in accordance with the present invention, may be effected in a reactor which is pressure sealable during conversion but which may be opened for recovery of the resin product after a predetermined reaction time. The process may thus be a batch process wherein conversion at elevated temperature and pressure is effected once the reactor is sealed. In accordance with the present invention the reactor may be sized and the amount of reactants determined so as to provide a void space in the reactor during reaction. In the case, for example, wherein the material having the denotable iodine-member is a sludge of alkali metal/$I_2$ and water, the weight ratio of sludge to resin may be 1:1 or higher, eg. 1:1 to 5:1; a weight ratio of 1:1 (if Amberlite 401-S is used as the resin) is preferred so as to minimize the amount of unabsorbed iodine which must be washed from the iodine/resin product.

The high temperature/pressure contact conditions may as mentioned above be chosen with a view to maximizing the iodine content of the obtained iodine (e.g. iodine) demand resin.

In accordance with the present invention conversion of the resin to a polyhalide (e.g. $I_3^-$) form may be effected at elevated temperature greater than 100° C., for example in the range of 105° C. to 150° C. (e.g. 110–115° C. to 150° C.); the upper limit of the temperature used will, for example, depend on the characteristics of the resin being used, i.e. the temperature should not be so high as to degrade the resin.

As mentioned in order to effect the conversion at elevated pressure, the conversion may take place in a closed vessel or reactor. The pressure in such case may be a function of the temperature such that the pressure may vary with the temperature approximately in accordance with the well known gas equation PV=nRT, wherein V=the constant (free) volume of the reactor, n=moles of material in the reactor, R is the universal gas constant, T is the temperature and P is the pressure. In a closed vessel, the temperature of the system may therefore be used as a means of achieving or controlling the (desired) pressure in the vessel depending upon the makeup of the Iodine mix in the reactor. Thus in accordance with the present invention, a reaction mix disposed in a pressure sealed reactor may be, for example, subjected to a temperature of 105° C. and a pressure of 200 mmHg, the pressure being induced by steam.

Alternatively, a relatively inert gas may be used to induce and\or augment the pressure in the reactor. Thus, a pressurized relatively inert gas may be injected into a sealed reactor. The chosen gas must not unduly interfer with the production of a suitable iodinated resin. The high temperature/pressure treatment may be conducted in a closed reactor in the presence of (trapped air), a non-interfering gas such as iodine itself or of some other relatively inert (noble) gas; the pressure as mentioned above may be augmented by the pressuring gas. Air, carbon dioxide, nitrogen or the like may also be used as a pressuring gas, if desired, keeping in mind, however, that the use thereof must not unduly interfer with the production of a suitable iodinated resin. If pressure is to be induced by steam then as mentioned below steps should be taken to isolate the reaction mix from (excess) water.

In accordance with the present invention, the elevated pressure is any pressure above ambient. The pressure may, for example, be 1 psig or higher, e.g in the range from 5 to 50 psig; the upper limit of the pressure used will also, for example, depend on the characteristics of the resin being used, i.e. the pressure should not be so high as to degrade the resin.

The residence or contact time at the elevated conditions is variable depending upon the starting materials, contact conditions and amount of (tenaciously held) iodine it is desired to be absorbed by the anion exchange resin. The contact time may thus take on any value; usually, however, it is to be expected that it will be desired that the contact time (under the conditions used) be sufficient to maximize the amount of (tenaciously held) iodine absorbed from the material containing the absorbable iodine moiety. The residence time may for example be as little as 5 to 15 minutes (in the case where a preimpregnation step is used as shall be described below) or several hours or more (up to 8 or 9 hours or more). The residence time exploited for elevated the conditions, in any event, will as mentioned above depend on the starting material, temperature and pressure conditions, etc. . . . ; it may vary from several minutes to 8 or 9 hours or more; the upper time limit will in any event also, for example, depend on the characteristics of the resin being used, i.e. the residence time should not be so high as to degrade the resin.

Preferably, the contact at high temperature/pressure is preceded by an initial impregnation or absorption step (first stage). Such first stage may be carried out for only a few minutes (e.g. for from 1 to 10 minutes or more) or for up to 24 hours or more (e.g. for from one hour or more i.e. for from three to twenty-four hours). The time period of the initial stage may be relatively short. The time period, for example, may be a few minutes or so and may correpond to the time necessary to just mix the reactants together; in this case the conversion may be considered to be essentially carried out in a single stage at elevated conditions. The residence time of the first stage will also be predetermined with a view to the end product resin desired. For example, a water containing sludge of triiodide ions can be contacted with a salt form of the starting resin at ambient (i.e. room) temperature and pressure conditions to obtain an intermediate iodide-resin reaction product including residual iodine-substance. This step is preferably carried out in a batch reactor; the obtained intermediate composition comprising an intermediate iodide-resin may then be subjected to the higher temperature and pressure in accordance with the present invention in batch fashion as well. Such a first stage may be used to initiate buildup of iodine within the resin matrix.

In accordance with the present invention an iodide-resin demand disinfectant may, for example, be obtained by a) bringing a porous, granular, starting resin into contact with an aqueous sludge of iodine and potassium iodide so as to obtain a paste mixture, iodine being present in the sludge essentially as triiodide ions, said starting resin being a strong base anion exchange resin having strongly basic groups thereof in a salt form the anion of which is exchangeable with triiodide ions, b) subjecting the paste mixture to elevated temperature and pressure conditions in an enclosed container or reactor (e.g. autoclave) for a predetermined impregnating duration of time, a void space being provided in the reactor such that contact occurs under an (essentially) iodine (rich) atmosphere, and c) washing the obtained iodide-resin product (with a suitable (i.e. purity) washing liquid, (e.g. deionised water, R/O water (at 45° C.), etc.) to remove water elutable iodine such as KI from the surface of the resin so that on drying no iodine (KI) crystals will form on the surface of the iodine/resin; R/O water, is water obtained using double reverse osmosis. R/O water is defined below.

More particularly an iodide/resin demand disinfectant may be obtained using the following sequence of steps:

1. The resin is purified by triple passage of water and then disposed in ethanol in an electrosonic bath and flushed with water and drip dried;

2. (Essentially) stoichiometric amounts of $I_2$ and potassium iodide are admixed with a minimum amount of water which is just sufficient to obtain an $I_3-$ slurry or sludge (with, if desired, very low heating);

3. The resin is admixed with the above-minimal water slurry in small aliquats so as to obtain a predetermined weight ratio of slurry to resin (e.g. a 50:50 weight ratio);

4. The resin-slurry mixture is then placed in a shaking bath at atmospheric pressure in a closed, air-tight container (if necessary the container being provided with a small pressure release valve or opening the purpose of which will be hereinafter explained) for a predetermined time period (e.g. for up to, for example, sixteen to twenty-four hours or more [e.g. a week if desired]) to form an intermediate resin composition;

5. The container containing the reaction mixture is then disposed in a (steam) autoclave and heated at high temperature, (e.g. 120° C.) to provide a super atmospheric pressure therein (with the small valve open if the container walls would not be able to resist the pressure to be exerted within the autoclave) for a predetermined residence time (e.g. a residence time of about fifteen minutes) calculated from the time the mixture reaches the predetermined high temperature (e.g. 120° C.).

6. The autoclave is removed from the heat and as soon as the pressure is equalized to atmospheric, the internal container is removed and the resin product is washed (e.g. six times) with R/O water until the wash water comes out with a total iodine content of less than 0.1 parts per million.

A small hole is necessary when a container such as a glass flask is used in order to avoid a too great pressure difference being built up between the interior of the flask and the interior of the autoclave which might cause the flask to collapse. The hole in any event is just large enough to more or less allow for the equalization of pressure and to maintain a positive pressure in the flask relative to the interior of the autoclave such that any foreign material such as water vapour is inhibited from flowing into the flask. A more sturdy pressure resistant container could of course be used such that, depending on the construction of the container and the temperature/pressure conditions prevailing in the autoclave, the hole may be avoided. Alternatively, instead of using a separate container to hold the reaction mix and placing it in a separate autoclave, a single autoclave/container may be used serving to hold and heat the reaction mix under pressure; such a container must of course be constructed so as to be able to resist the predetermined reaction conditions.

The iodide-resin compound formed as described herein can be used as a demand disinfectant to disinfect water by batch contacting the contaminated water with the resin; continuous processing as mentioned in U.S. Pat. No. 3,923,665 is also possible. Thus water containing viable bacteria (to be killed) may be passed through a fixed bed of porous granular iodine/resin material. The maximum permissible flow rates for total bacterial sterilization may vary with the concentration of the polyiodide (e.g. triiodide) groups in the resin, bed depth, bacterial count, etc. . . . The disinfection process may be monitored by taking samples of water after passage through the bed. Potable innocuous water may thus be readily produced in accordance with the present invention without the incorporation of objectionable amounts of free iodine therein as a result. The resin may be used with any (known) water treating devices such as for example those shown in U.S. Pat. Nos. 4,749,484 and 4,978,449.

In accordance with a further aspect, however, as mentioned above, the present invention also provides a method for disinfecting air containing airborne microorganisms. The method may comprise passing the air over a demand disinfectant resin such that airborne microorganisms contact said resin and are devitalized thereby, the demand disinfectant resin comprising an iodinated strong base anion exchange resin. The method may, for example, include passing the air through a bed of granules of iodinated resin so that the air courses over the granules (in a serpentine manner) as the air makes its way through the bed. The maximum permissible flow rates for total bacterial sterilization may vary with the concentration of the polyiodide groups in the resin, bed depth, bacterial count, etc. . . . The iodinated strong base anion exchange resin may comprise a strong base anion exchange resin component which represents from 25 to 90 (preferably 45 to 65) percent by weight of the total weight of the iodinated resin.

In accordance with an additional aspect, the present invention provides a system for disinfecting air containing airborne microorganisms, said system, for example, comprising means for providing an air path for the movement of air therethrough, and a demand disinfectant resin disposed in said air path such that airborne microorganisms in air passing through said air path are able to be brought into contact with said resin and be devitalized thereby, said demand disinfectant comprising an iodinated strong base anion exchange resin.

An air path means may define an air inlet and an air outlet. The resin may be disposed between said inlet and outlet or be disposed at the inlet or outlet. The air path means may take any form. It may take the form of ductwork in a forced air ventilation system with the demand disinfectant comprising a bed of resin granules through which the air is made to pass, the bed otherwise blocking off the air path. Alternatively the air path means may be defined by a cartridge used for a gas mask, the cartridge having an inlet and an outlet for air; the iodinated resin for the cartridge may, if desired, be present as a bed of granules, granules incorporated into a (fluid) porous carrier (e.g. tissue, polyurethane foam, etc.) or alternatively take a more massive form such as a plate(s), a tube(s), a block(s), etc. . . . Cartridge type gas masks are known; such gas masks may be obtained for example from Eastern Safety Equipment Co., Mosport, N.Y., USA.

Figure 4:
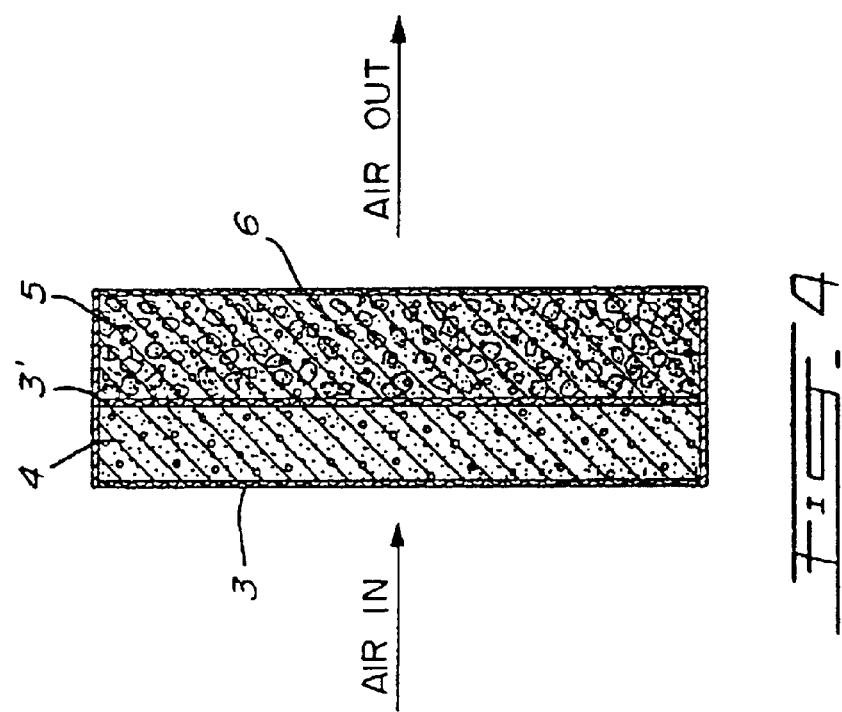
FIG. 4 is a cross sectional view 4—4 of the cartridge of FIG. 1.
Figure 3:
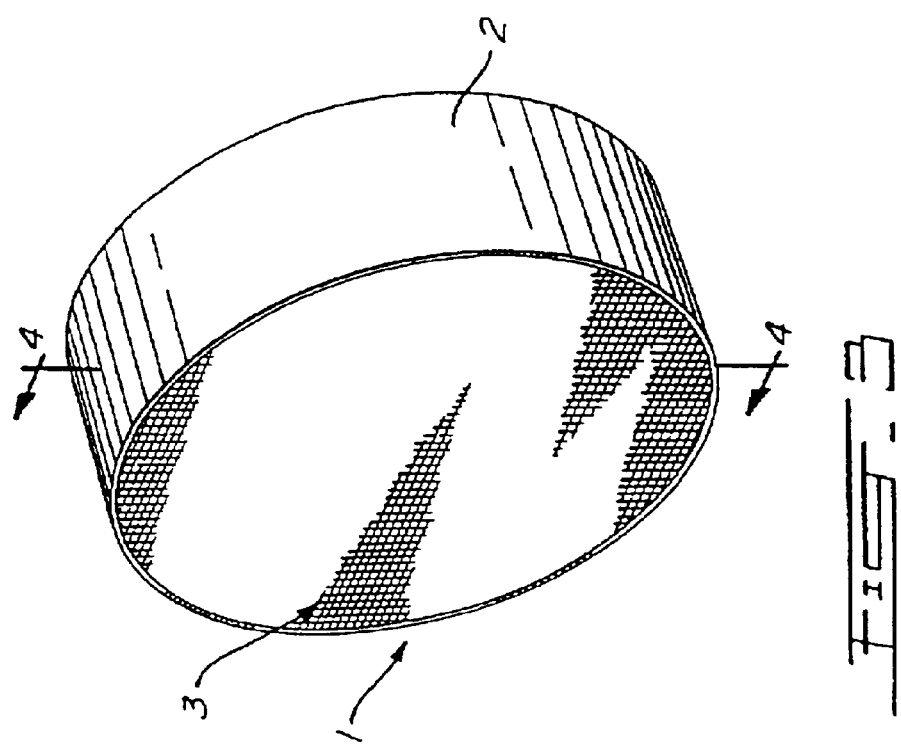
FIG. 3 is a perspective view of a cartridge which may be used to house an iodinated resin as described herein for use for example in a gas mask.

The C-50 cartridge from a gas mask (from Glendale Protecting Technologies Inc. Woodbury, N.Y., USA) may for example be adapted to hold a bed of resin of granules of the present invention. Referring to FIG. 3, the cartridge 1 comprises an a hollow, open ended, thi-walled, tubular body of circular cross section. The wall 2 may for example be of nylon. The open ends of the cartridge are each blocked off by some suitable mesh like support material 3 (e.g. 10 micron polypropylene mesh) which is held in place in any suitable known manner such as by glues, spring clip, etc. Referring to FIG. 4, the iodinated granular resin bed 4 occupies the entire space between the mesh supports 3 and 3'; although the granular resin is more or less tightly packed between the mesh supports 3 and 3', there are still air spaces between the granules for the passage of air through the granular bed. The mesh supports each have openings small enough to retain the iodinated resin in place while allowing air to pass therethrough into the and through the supported resin bed 4. The cartridge as shown in FIG. 4 may include a downstream bed 5 of granules of activated carbon, catalyst, or iodine absorbent resins, to scavenge any iodine liberated from the iodinated resin 4. The activated carbon bed 5 is held in place by a mesh support 3' and an additional mesh 6. The bed depth of the resin and carbon is shown as about 2.5 cm; wheras the bed diameter is about 8 cm. If the iodinated resin made in accordance with the process of the present invention is used the carbon bed may be omitted, i.e. only the iodinated resin bed 4 may be present in the cartridge as the active component (in the examples below, unless the contrary is indicated, the cartridges do not include any carbon bed); in this case the bed depth may, for example, be less 2.5 cm, e.g. 0.1 cm, 0.25 cm, 0.5 cm, 0.85 cm, 1.15 cm, etc. . . . Such a cartridge may be disposed in an air path as shown for example in FIGS. 5 and 6 which will be discussed below.

The resin disposed in the air path could of course take on any form other than granules such as blocks, plates, tubes etc. . . .

The iodinated demand disinfectant resin for air treatment may be any (known) iodinated resin so long as the iodinated resin is capable of devitalizing airborne microorganisms (i.e. microorganisms transported by air) coming into contact therewith. It may, for example, be a resin as proposed in U.S. Pat. Nos. 3,923,665 and 4,238,477; in this case, however, it may be necessary to use the resin in conjunction with an iodine scavenging material if the resin gives up too much iodine to the air. The iodine scavenging material may be an activated carbon material or an un-iodinated strong base anion exchange resin as described herein.

Alternatively, as mentioned above, iodinated resin may advantageously be a resin made in accordance with the present invention; in this case the resin need not be used in conjunction with an iodine scavenging material such as a (known) exchange resin, activated carbon, catalyst, etc., since an iodinated resin made in accordance with the process of the present invention may liberate iodine into the air in an amount below acceptable threshold limits for breathing by human beings.

If desired the iodinated resin for the treatment of air or water may be some type of mixture of iodinated resins, e.g. a mixture of a known iodinated resin and an iodinated resin prepared in accordance herewith.

As mentioned above, the present invention in a further aspect provides a combination which may act as a sterilization barrier with respect to microorganisms. The sterilization combination may, for example, be incorporated into protective wearing apparel or be configured as a sterilization dressing for lesions such as for example, wounds and burns; the sterilisation barrier combination can be configured to be or not to be air breathable.

A sterilization dressing of the present invention advantageously may take the form of a flexible porous cellular polymeric foam sheet having a spongy aspect and having dispersed within the polymeric matrix thereof particles of a demand disinfectant comprising a (known) iodinated resin or an iodinated resin as described herein. The sterilization sheet may be placed over a burn area to maintain the burn area in a sterilized state during the healing process. The disinfectant particles are distributed throughout the polymeric matrix and have surfaces projecting into the open pores of the spongy matrix; the spongy matrix acts as a sponge so that on the body side thereof it can soak up fluid such as pus which exude from the burn lesion. Once within the body of the matrix any microorganisms in the fluid or pus can contact the disinfectant resin particles and become devitalized as a result. On the other hand, any microorganisms on the opposite side of the sterilization barrier which attempt to pass through the barrier are also subject to being contacted with the disinfectant and are also devitalised.

A (flexible) phamaceutically acceptable hydrophilic foam matrix may be obtained by reacting water with HYPOL foamable hydrophilic polyurethane polymer; the HYPOL polymer starting material may be obtained from W. R. Grace & Co. Lexinington Mass. U.S.A. Water reacts to cross link the HYPOL polymer; if water is added quickly or at relatively high temperature foaming occurs and a foam product is obtained.

The carrier component may, as necessary, also be oil or fat loving, e.g. for dealing with individuals with high cholesterol levels.

If desired the iodinated resin for the sterilisation combination may be some type known iodinated resin, a resin prepared in accordance herewith, or a mixture of iodinated resins, e.g. a mixture of a known iodinated resin and an iodinated resin prepared in accordance herewith.

FIGS. 7 to 11 which illustrate a number of example embodiments of sterilisation barrier combinations of the present invention will be discussed below; these combinations are also described in example 15 below.

Turning back to the process of the present invention, if commercially available materials are to be used to make the iodine/resin then, depending on the purity thereof, the starting materials may have to be treated to remove components which may interfer with the absorption of the halide into the resin. Water if present in the initial reaction mix should be free of interfering elements such as interfering ions. Distilled or ion free water is preferably used for washing.

The following materials may be used to prepare a triiodide resin in accordance with the present invention:

a) Amberlite 401-S (from Rohm & Hass) a strong base anion exchange resin in granular form, having the following characteristics:

support matrix—styrene/divinyl benzene polymer anion—chlorine density—1.06 effective size (diameter)—0.52 mm total exchange capacity—0.8 meq/ml working Ph range—0 to 11 moisture content—62% working temperature—170° F. or less b) $I_2$ (solid)—U.S.P. grade (from Fisher Scientific)

c) Potassium iodide (KI)—U.S.P. grade (from Fisher Scientific)

d) Water—ultra pure: obtained using double reverse osmosis (i.e. herein sometimes referred to simply as R/O water)

e) Ethanol—U.S.P. grade (from Fisher Scientific)

Using the above substances a resin cramed with triiodide (i.e. a triiodide jam-backed resin) may be obtained as indicated in the following examples.

For the following examples, the following procedure for the evaluation of iodine ($I^2$) and Iodide ($I^-$), was conducted according to "standard methods for the examination of water and wastewater 17e Ed.":

Iodine method: mercuric chloride added to aqueous elemental iodine solutions causes complete hydrolysis of iodine and the stoichiometric production of hypoiodous acid. The compound 4, 4', 4"methylidynetris (leuco crystal violet) reacts with the hypoiodous acid to form crystal violet dye. The maximum absorbance of the crystal violet dye solution is produced in the Ph range 3.5–4.0 and measured at a wavelength of 592 nm. The absorbance follows beers' law over a wide range of iodine concentration. Iodine can be measured in the presence of max. 50 PPM iodide ions without interference.

Iodide method: iodide is selectively oxidized to iodine by the addition of potassium peroxymonosulfate. The iodine produced reacts instantaneously with the indicator reagent leuco crystal violet over the same conditions described previously for iodine methods. Total iodine+iodide results from this procedure and iodide is calculated from substraction of iodine concentration.

Readings were performed on a 1 kb spectrophotometer with a lightpath of 1 cm and selected at 592 nm.

EXAMPLE 1

Starting Materials Pretreatment i) Resin

The resin is water washed to remove undesirable elements such as material in ionic form. Thus, 100.00 grams of Amberlite 401 S and 200 ml of R/O water are placed in an erlennyer of 1000 ml. The mixture is shaken for about 3 minutes and the water is then separated from the resin by drip filtration using a wathman filter paper and funnel. The resin is water washed in the same fashion two more times. After the last water wash the resin is drip dried (i.e. again using a wathman filter paper and funnel) for 15 minutes.

The so recovered water washed resin is subjected to an alcohol wash to dissolve undesirable organic material which may be stuck on the resin. Thus, the water washed resin is immersed in 300.00 ml of ethanol. The resin alcohol mixture is shaken in an ultrasonic bath (Crest ultrasonic: 1000 Watts—20 liter capacity) for 5 minutes. The alcohol washed resin is drip dried, again using a wathman filter paper and funnel.

The "fish" smell is removed from the alcohol washed resin by a final water washing stage wherein the wash R/O water is preheated to 40 degrees celsius. The alcohol washed resin is placed in an erlenmyer flask (1000 ml) and 250 ml of R/O water at 40 degrees celsius is added thereto. The water-resin mixture is shaken in a shaking bath (Yamata shaking bath—1 impulse per second/water at 32 degrees celsius) for 5 minutes; the water is then removed from the resin by drip drying as mentioned above. The water wash is repeated once more and the resin is drip dried (for 1 hour) as mentioned above. The washed resin is now ready for use in example 2 hereinbelow.

ii) Iodine Sludge Containing Water

A mixture of iodine ($I_2$) and potassium iodide (KI) is prepared by mixing together, in an erlenmyer flask, 60.00 grams of iodine and 40.00 grams of potassium iodide (in both cases on a dry weight basis). Thereafter R/O water is admixed slowly drop by drop with the mixture until a metallic looking sludge is obtained (e.g. with the addition of about 5.00 grams of water). The obtained iodine/potassium iodide sludge is then ready for use in example 2 hereinbelow.

EXAMPLE 2

Low Temperature/Pressure Preimpregnation of Resin with Iodine

The aqueous iodine sludge, as obtained above, is placed in a 500.00 ml Erlenmyer flask and is slowly heated to, and maintained at 40 degrees celsius for a few minutes. Once the temperature of the sludge reaches 40° C., the washed resin, obtained as above, is slowly admixed with the iodine sludge in 10.00 gram portions every 8 minutes until all of the washed resin is within the erlenmyer flask. The 500 ml Erlenmyer flask, containing the obtained starting mix (comprising the $I_2$/KI mixture and the washed resin—approximately 100 grams of each of the starting materials), is then sealed with a cork and is placed in a shaking water bath (Yamato BT: –25) for a period of 16 hours. The temperature of the water in the shaking bath is maintained at about 20 degrees celsius during this time period. At the end of the time period, the Erlenmyer flask is removed from the shaking bath; at this point the removed flask contains an preimpregnation mix comprising impregnated resin and remaining $I_2$/KI. The Erlenmyer flask is sized such that at the end of this (initial) impregnation step, it is only 50% filled with the in process resin, etc, i.e. there is a void volume above the impregnation mix.

NOTE: If processing of the treated resin is stopped at this point and the obtained resin is suitably washed, a resin is obtained in accordance with the prior art i.e. U.S. Pat. No. 3,923,665.

EXAMPLE 3

Elevated Pressure/Temperature Treatment

The cork of the Erlenmyer flask of EXAMPLE 2 removed from the shaking bath and including the obtained impregnation nix comprising impregnated resin and remaining $I_2$/KI, is changed for a cork having a small diameter perforation passing therethrough (i.e. of about 3 mm in diameter). With the perforated cork in place, the Erlenmyer flask is disposed within a (steam pressure) autoclave along with a suitable amount of water. With the autoclave (pressure) sealed about the flask, the autoclave is heated. Heating proceeds until an internal temperature and pressure of 115 degrees Celsius and 5 psig respectively is reached. Once those parameters have been reached, they are maintained for 15 minutes of processing time. Thereafter the autoclave is allowed to slowly cool for 50 minutes of cooling time (until the internal pressure is equal to ambient pressure) before removing the Erlenmyer flask containing a (raw) product resin demand disinfectant in accordance with the present invention.

EXAMPLE 4

Washing of Raw Product Resin

The (raw) disinfectant of Example 3 is removed from the autoclave Erlenmyer flask and placed in another 2000 ml Erlenmyer flask. 1400 ml of R/O water at 20 degrees Celsius is admixed with the resin in the flask and the slurry is shaken manually for 3 minutes. The wash water is thereafter removed from the flask by decantation. This wash step is repeated 7 more times. The entire wash cycle is repeated twice (i.e. eight water washes per cycle) but using water at 45 degrees Celsius for the next wash cycle and then with water at 20 degrees Celsius for the last wash cycle. The washed iodine-resin is then ready to use.

EXAMPLE 5

Comparative Physical Data

The following resins were examined with respect to certain physical characteristics:

Resin I-A:

Iodinated resin manufactured in accordance with the present invention i.e. as obtained from example 4 above.

Resin I-B:

Iodinated resin manufactured in accordance with teachings of the prior art (i.e. U.S. Pat. No. 3,923,665), namely as obtained from example 2 above after suitable washing to remove elutable iodine.

Resin I-C:

Iodinated resin manufactured by Water Technology Corporation in Minneapolis (a triiodide based disinfectant resin).

Resin I-D:

Iodinated resin manufactured by Water Technology Corporation in Minneapolis, sold under the Trademark: Pentapure.

In the examples which follow the above resins will be referred to using the above designations, i.e. I-D, Resin I-A, etc.

EXAMPLE 5.1

Comparative Wet Tap Density

The resins were examined in a drip dried state, i.e. the resins were used after being drip dried using wathman filter paper and a funnel (for a 5 minute dry period). 25 ml and 100 ml flasks were used for the study. The flaskes were weighed empty. The flasks were then filled with resin and were then subjected to a manual vibration sequence (approximately 2 impulses per second for two minutes) in order to settle the resin, the volume of the settled resin was then noted. The density was obtained by weighing a filled flask and subtracting the weight of the empty flask so as to obtain the weight (grams) per unit volume (ml) of the resin. The results are shown in Table 1 below.

TABLE 1

| Resin | density |
|---|---|
| I-A | 1.720 gm/ml |
| I-B | 1.480 gm/ml |
| I-D | 1.600 gm/ml |

EXAMPLE 5.2

Comparative Dry Tap Density

The same procedure as described above for example 5.1 was used except that the initial resin materials were dried simultaneously for 12 hours at 55 degrees Celsius, and placed in desiccant for 2 hours during cooling. The results are shown in Table 2 below.

TABLE 2

| Resin | Desity |
|---|---|
| I-A | 1.088 gm/ml |
| I-B | 0.957 gm/ml |
| I-D | 1.016 gm/ml |

EXAMPLE 5.3

Iodine Content 1.0 gm of each of the different resins was boiled in 20 ml of water with a concentration of 5% by weight of sodium thiosulphate. Boiling was conducted for 20 minutes whereafter the water mixture was set aside to air cool for 12 hours. The resin was then recovered and washed with 50 ml of a boiling water solution of sodium thiosulphate. Thereafter the resin was dried in an oven for 12 hours at 105 degrees. The iodine desorbed resin was weighed in each case and the weight difference was used to calculate the % by weight of the initial resin represented by the active iodine removed. The results are shown in Table 3 below.

TABLE 3

| Resin | % by weight iodine |
|---|---|
| I-A | 43.7% |
| I-B | 32.4% |
| I-C | 30.7% |
| I-D | 36.7% |

NOTE:
As may be seen from Table 3, the resin in accordance with the present invention (i.e resin I-A) has a substantially higher iodine content than the commercially available resins or the resin prepared in accordance with the prior art (i.e. resin I-B).

EXAMPLE 5.4

Comparative Iodine Content in Water During Stagnation 100.00 gm of each resin was mixed with 125 ml of water in Erlenmyer flask which was sealed airtight. The water mixture was allowed to stand 20 degrees Celsius for 7 days. A water sample was then taken from each water mixture and subjected to a standard method for testing water for the presence of Iodine using the Leuco Crystal Violet Iodometric Spectrophotometer Technique so as to obtain the "ppm" concentration of iodine in the water. The results are shown in Table 4 below.

TABLE 4

| Resin | bleed iodine concentration (ppm) |
|---|---|
| I-A | 1.7 ppm |
| I-D | 2.5 ppm |

NOTE:
As may be seen from table 4, the resin of the present invention (resin I-A) has a significantly lower iodine bleed lose into water than the commercial product (resin I-D).

EXAMPLE 5.5

Resin Size Study

Two grams of dry resin was examined with a microscope having a micrometer scale system and sized by eye. The results are shown in Table 5 below.

TABLE 5

| Resin | Size (ie. approximate effective diameter size) - lowest to highest |
|---|---|
| AMBERLITE I 401 S | 0.35 mm to 0.52 mm |
| I-A | 0.60 mm to 1.20 mm |
| I-B | 0.40 mm to 1.00 mm |

EXAMPLE 6

Simultaneous tests were conducted to compare the antimicrobial activity of a disinfectant resin in accordance with the present invention (resin I-A, above) and a prior art disinfectant resin (resin I-D, above). A series of batch solutions was prepared; each batch solution contained a different microorganism. A batch solution was divided into test portions so that the comparative tests could be carried out against each of the resins at the same using a respective test portion of the batch solution; the volume of the test portions was 150 liters. The same amount of each of the resins was supported in a respective fixed bed configuration (i.e. the resins were disposed in a cylinder 1 cm high having an internal diameter of 3 cm). The respective test solutions were allowed to pass downwardly through each of the resins in the same fashion and at the same flow rate (i.e. the test conditions were the same for each resin). The tests were carried out at ambient conditions of temperature and pressure. The microorganisms and test results were as follows:

a) A lyophilized strain of *KLEBSIELLA TERRIGENA* (A.T.C.C. 33257) was rehydrated in phosphate-buffered saline (PBS) and was subcultivated in order to obtain a broth with a bacterial density of $10^9$ cfu/ml (cfu=colony forming units). The broth was treated to obtain media free monodispersed bacterial cells. The bacterial solution was then diluted in water to provide the test batch solution at an initial concentration of $4.8 \times 10^7$ cfu per 100 ml.

Microbiological monitoring of the test water was done throughout the experiment. Sampling of the filtered water was done at intervals prescribed by the: U.S.E.P.A. (protocol section 3.5.1 d 1(b)) with the membrane-filter technique for *KLEBSIELLA* described in: 17th edition of Standard Methods for the examination of water and wastewater, pp. 9–97 to 9–99.

A test solution containing *KLEBSIELLA TERRIGENA* (A.T.C.C. 33257) at an initial concentration of $4.8 \times 10^7$ per 100 ml was passed through the fixed bed of each resin at a flow rate of 125 ml/min to 200 ml/min. The treated volume of solution for each resin was 150 liters in total. Sampling of the effluent or treated solution was effected at intervals corresponding with a predetermined percentage of the test portions having passed through the resins. The results are shown in Table 6a below:

TABLE 6a

| Total % of test solution passed through the resin | Microorganism concentration in test effluent for each resin type (cfu/ml) | |
|---|---|---|
| | Resin I-D | Resin I-A |
| 0% | 0/0/0 | 0/0/0 |
| 25% | 0/0/0 | 0/0/0 |
| 50% | 0/0/0 | 0/0/0 |
| 60% | 0/0/0 | 0/0/0 |
| 75% | 0/0/0 | 0/0/0 |
| 90% | 0/0/0 | 0/0/0 |
| 100% | 0/0/0 | 0/0/0 |

As may be seen from table 6a the destruction of the bacteria was total in the case of each resin.

b) Poliovirus 1 (A.T.C.C VR-59) was obtained as a lypholized pellet, rehydrated in PBS, and grown on buffalo green monkey (BGM) kidney cells from the Armand Frappier Institute (IAF) in Laval Quebec. Standard cell culture and virological procedures were used to obtain a concentration of $3 \times 10^7$ of monodispersed virion particles per ml. Enough virus was added to a holding tank to obtain a concentration of about $1 \times 10^7$ pfu per liter for the test batch solution (pfu=plaque-forming units).

The assay technique consisted of inoculating healthy BGM cells with a small amount of filtered water at regular intervals. If a virus particle were present, a plaque would be observed on the cellular bed thru the gellified maintenance media which contained a vital stain.

A test solution containing Poliovirus 1 (A.T.C.C VR-59) at an initial concentration of $1 \times 10^7$ pfu per liter was passed through the fixed bed of each resin at a flow rate of 125 ml/min to 200 ml/min. The treated volume of solution for each resin was 150 liters in total. Sampling of the effluent or treated solution was effected at intervals corresponding with a predetermined percentage of the test portions having passed through the resins. The results are shown in Table 6b below:

TABLE 6b

| Total % of test solution passed through the resin | Virus concentration in test effluent for each resin type (pfu/l) | |
|---|---|---|
| | Resin I-D | Resin I-A |
| 0% | 0/0/0 | 0/0/0 |
| 25% | 0/0/0 | 0/0/0 |
| 50% | 0/0/0 | 0/0/0 |
| 60% | 0/0/0 | 0/0/0 |
| 75% | 0/0/0 | 0/0/0 |
| 90% | 0/0/0 | 0/0/0 |
| 100% | 0/0/0 | 0/0/0 |

As may be seen from table 6b the destruction of the Poliovirus was total in the case of each resin.

c) Rotavirus (A.T.C.C VR-899) was obtained, rehydrated in PBS, and grown on A-104 cells obtained from IAF. The method used to obtain the diluted poliovirus above was used with respect to the *rotavirus*. The yield for rotavirus grown on MA-104 cells was $2 \times 10^6$ pfu/ml. After dilution in the holding tank the concentration of the virus was $1 \times 10^7$ pfu per liter.

The assay techniques were similar to those used for poliovirus, only the cell type and vital stain changed since they are specific for each type of virus. The same sampling strategy was applied.

A test solution containing *Rotavirus* (A.T.C.C VR-59) at an initial concentration of $1 \times 10^7$ per 100 ml was passed through the fixed bed of each resin at a flow rate of 125 ml/min to 200 ml/min. The treated volume of solution for each resin was 150 liters in total. Sampling of the effluent or treated solution was effected at intervals corresponding with a predetermined percentage of the test portions having passed through the resins. The results are shown in Table 6c below:

TABLE 6c

| Total % of test solution passed through the resin | Virus concentration in test effluent for each resin type (cfu/ml) | |
|---|---|---|
| | Resin I-D | Resin I-A |
| 0% | 0/0/0 | 0/0/0 |
| 25% | 0/0/0 | 0/0/0 |
| 50% | 0/0/0 | 0/0/0 |
| 60% | 0/0/0 | 0/0/0 |
| 75% | 0/0/0 | 0/0/0 |
| 90% | 0/0/0 | 0/0/0 |
| 100% | 0/0/0 | 0/0/0 |

As may be seen from table 6c the destruction of the Rotavirus was total in the case of each resin.

EXAMPLE 7

An iodine bleed test was conducted on the Resin I-A and Resin I-D mentioned above. The tests were conducted as follows:

A pressure syringe was filled with 20 grams of resin (inner chamber of 3 cm×13 cm). Using a peristaltic pump 750 ml/min of R/O water (sterilized) was pumped through the syringe; the resin being maintained in the syringe by suitable mesh means. The total water passed through the resin was 5 liters.

Figure 1:
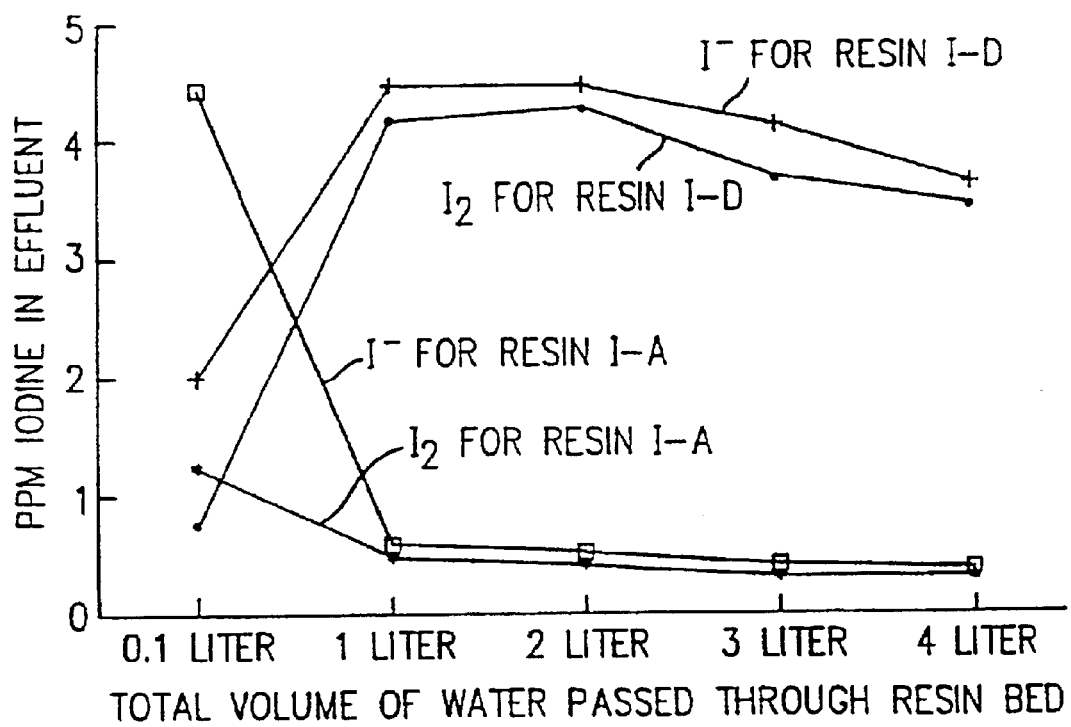
FIG. 1 is a graph of showing the ppm of Iodine in the effluent versus the total volume of water contacted with a disinfectant-resin bed of the prior art and an example disinfectant resin of the present invention.

The results of the tests are given in the graph shown in FIG. 1; i.e. ppm iodine in effluent vs total volume water passed through resin. The bleed test results as shown in the graph compares iodine ($I_2$) and iodide ($I^-$) in effluent of treated water after passing through each of the resins.

EXAMPLE 8

Figure 2:
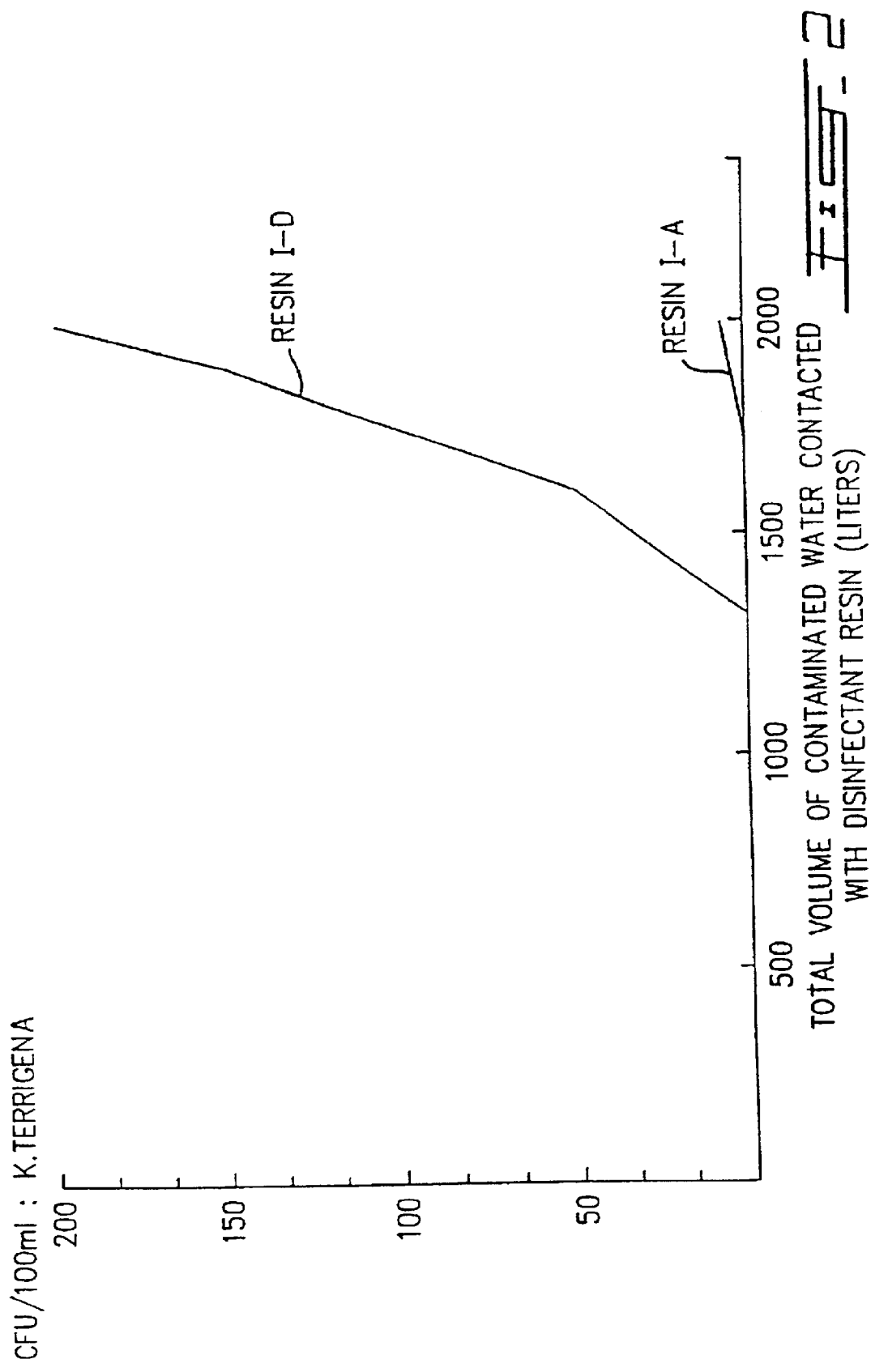
FIG. 2 is a graph of the number of microorganisms in effluent versus the total volume of contaminated water contacted with a disinfectant resin of the prior art and an example disinfectant resin of the present invention.

The bacteriocidal longevity of the Resin I-A and Resin I-D were determined for purposes of comparison. Two fixed resin bed devices were provided, one device loaded with one of the resins and the other device loaded with the other resin; each device was loaded with 75.00 grams of a respective resin. The tests for each resin bed were conducted simultaneously. For each resin bed, the solution to be treated was passed therethrough at a flow rate of 2.0 liters per minute, with an initial concentration of *Klebsiella Terrigena* $1\times10^7$ cfu/100 ml. The effluent was tested at intervals for the presence of viable bacteria. As may be seen in the graph of FIG. 2, the volume of contaminated solution at which bacteria start to pass through the prior art resin (i.e. Resin I-D) is significantly less than the breakthrough volume for the resin of the present invention (i.e. Resin I-A). From FIG. 2 it may be seen that the bacteriocidal activity of the disinfectant resin of the present invention (Resin I-A) is superior to that of the known resin (Resin I-D), i.e. the Resin I-A has about a 16% superior antimicrobial activity in relation to the amount of water treatable by a given amount of disinfectant resin.

EXAMPLE 9

Preparation of Resin I-A' of the Present Invention

An iodinated resin (Resin I-A') was prepared following the procedures of examples 1 to 4 except that for the resin, Amberlite IR-400 ($OH^-$) (was used and for the procedure of example 3 the elevated temperature and pressure conditions were set at 121° C. and 15 psig respectively. Resin I-A' was used in the following examples.

EXAMPLE 10

Comparative Iodine Content in Effluent Air

Two cartridges as illustrated in FIGS. 3 and 4 were prepared. Each cartridge contained 50.0 grammes of dry (granular) resin (i.e. and no activated carbon bed). One cartridge contained Resin I-A' and the other contained Resin I-D.

Figure 5:
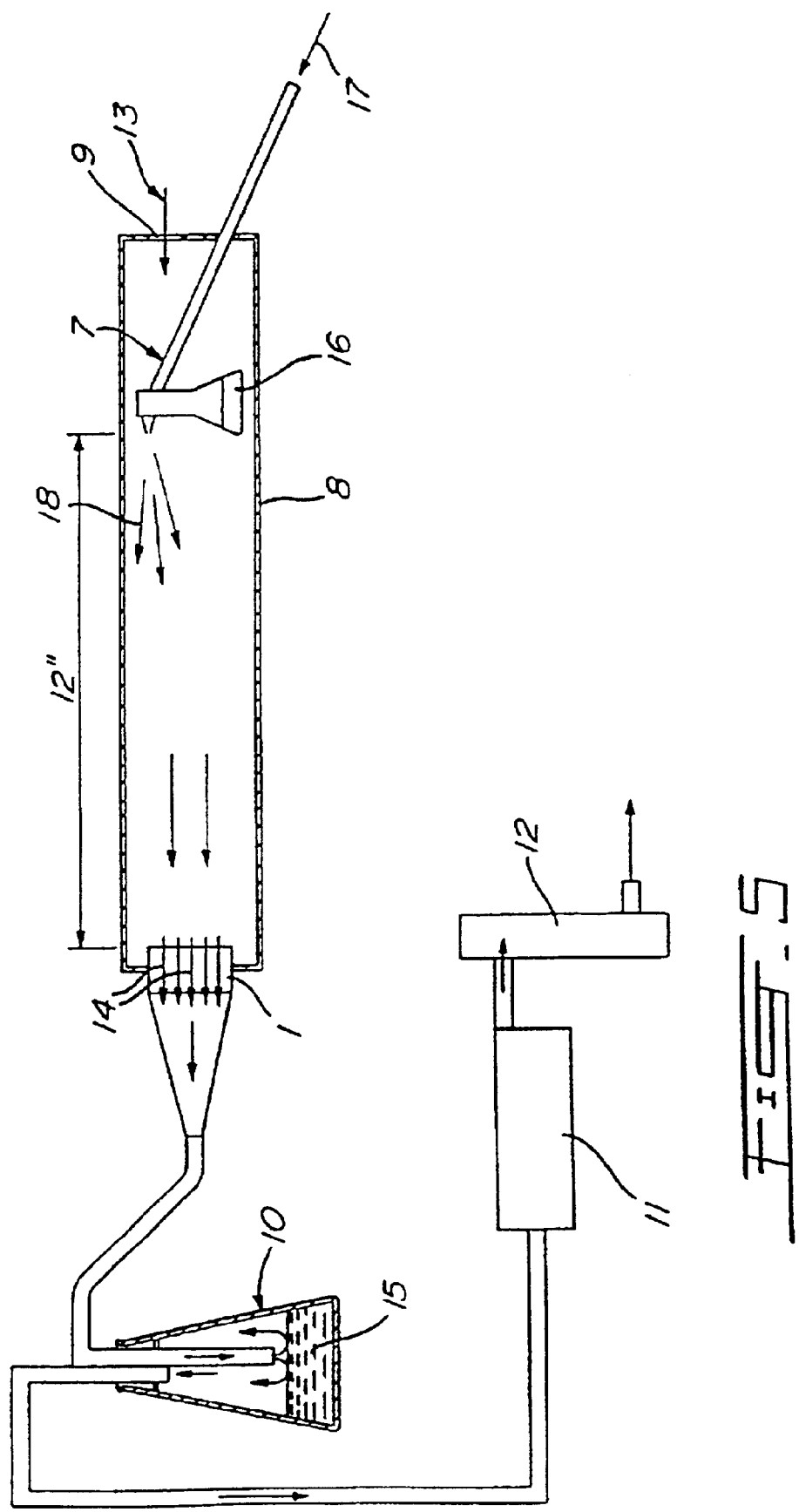
FIG. 5 is a schematic illustration of a system for testing a cartridge containing an iodinated resin.
Figure 6:
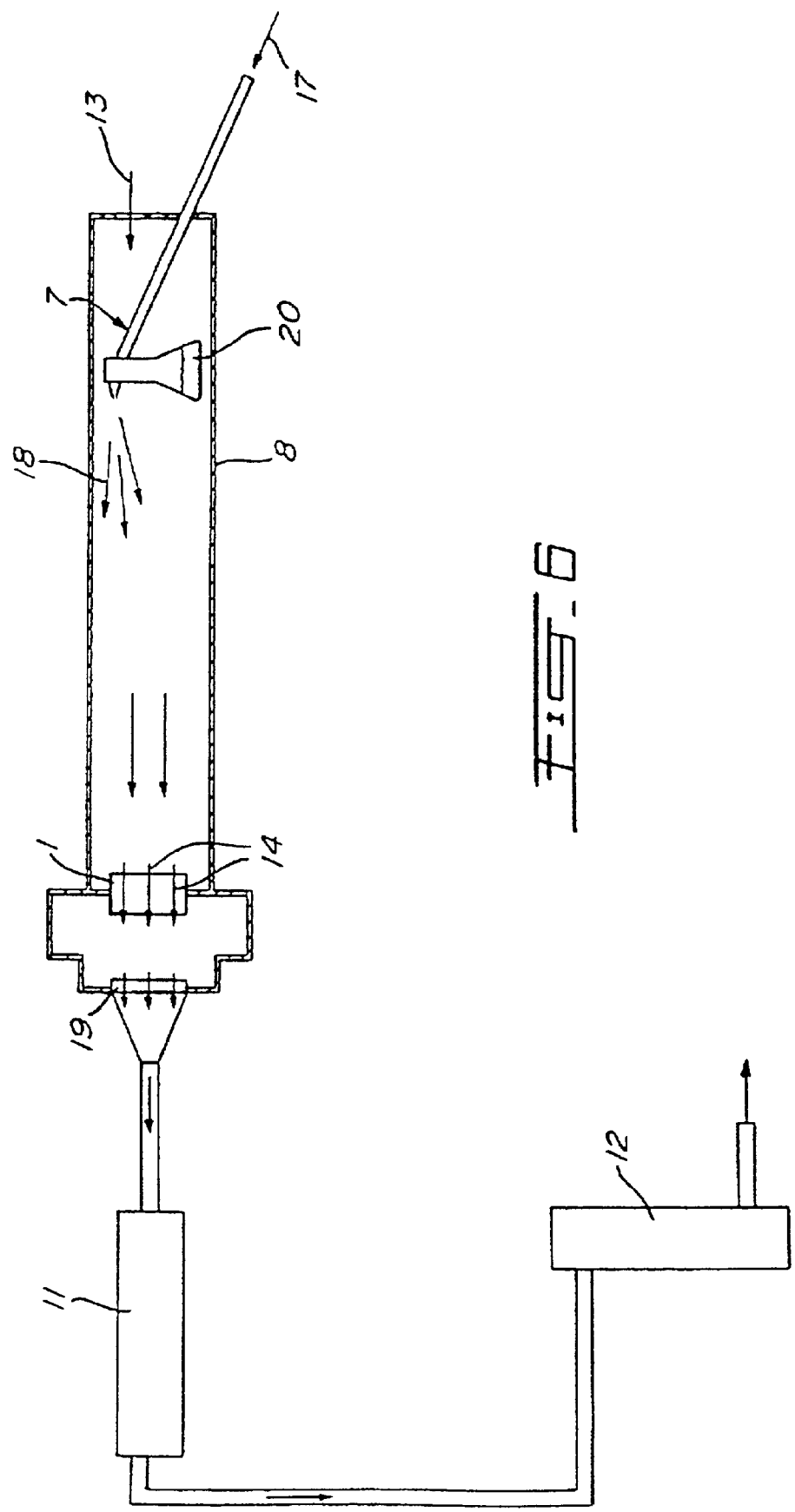
FIG. 6 is a schematic illustration of another type of system for testing a cartridge containing an iodinated resin.

The cartridges were each disposed in a system as illustrated in FIG. 5 but which did not contain any atomizer indicated generally by the reference number 7. The system included a housing 8 for defining an air path and had an air inlet 9. The resin cartridge 1 was disposed at the outlet of the air path. The air leaving the cartridge 1 was directed by appropriate tubing to a collector station 10. The system included a vacuum pump 11 (but not the air sterilizer system 12) for drawing air from inlet 9 through the system.

In operation a cartridge 1 was releasably placed in position (e.g. snap fit, etc.) and the vacuum pump activated so as to draw outside air (indicated by the arrow 13) into the housing 8. The air passed through the cartridge 1 as shown by the arrows 14. The air leaving the cartridge 1 was then directed to the collector station 10. The air entering the collector station 10 impinged upon a iodine collector solution 15 (comprising double reverse osmosis water, i.e. R/O water) in the collector station 10. Air leaving the collector station 10 thereafter passed through the pump 11 and was exhausted to the outside air.

Using the above described system, each, cartridge was submitted to an air velocity therethrough of 0.7 Liter/per minute for a period of 50 minutes. The collector station 10 included 50 ml purified R/O water (the water was then subjected to standard optical coloration techniques (i.e. the Leuco violet technique as referred to in example 5.4 above), to determine the total iodine content).

The results of the tests are shown in table 10a:

TABLE 10a

| Resin type | total iodine ($I_2$) |
|---|---|
| Resin I-A' | 0.4 ppm |
| Resin I-D | 1.1 ppm |

The results of the tests as shown in table 9a means that each gramme of both of the resin types will add a definite amount of iodine to the effluent air, namely as indicated in table 10b.

TABLE 10b

| Resin type | iodine ($I_2$) release per gram resin |
|---|---|
| Resin I-A' | 0.014 Mg/m³/gr |
| Resin I-D | 0.031 Mg/m³/gr |

Thus, for example, if a gas mask cartridge as discussed above contained 50.0 gm of iodinated resin, the resins would emit the level of iodine set out in table 10c below TABLE 10c

| Resin type | iodine ($I_2$) release |
|---|---|
| Resin I-A' | 0.7 Mg/m³ (= 50 gr × 0.014 mg/m³/gr) |
| Resin I-D | 1.5 Mg/m³ (= 50 gr × 0.031 mg/m³/gr) |

The "Committee of the American conference of governmental industrial hygienist." emits the "threshold limit value" or T.L.V. for common chemicals. The iodine T.L.V. is 1.0 Mg/m³ for air analysis for human breathing during a period of 8 hrs.

Thus, while the Resin I-D releases 50% more iodine than the maximum T.L.V. indicated above, the Resin I-A' (of the present invention) releases iodine at a level well below the T.L.V. The Resin I-A' could thus be used without an iodine scavenger; this would, for example, simplify the construction of a gas mask cartridge. The known Resin I-D on the other hand could also be used but it would require some sort of iodine scavenger (e.g. activated carbon) to obtain the necessary iodine T.V.L. level.

EXAMPLE 11

The Resin I-A' was Tested with Different Microorganisms Under Different Conditions for the Sterilization of Air

EXAMPLE 11.1

Direct Contact Sterilization Study

Resin I-A' was evaluated for its biocidal capacity on direct contact with *Klebsiella Terrigena* in relation to a time reference and a humidity content variation; namely water content variations of 110%, 50% & 0% (relative to the weight of dry resin) and time variations of 2, 5, 10, and 15 seconds.

After preparing the three resins with their respective humidity content 25 glass rods were sterilized. A vial containing 25 ml of the inoculum (*Klebsiella Terrigena:* $10^9 \times ml$) was also prepared.

The testing proceeded as follows with respect to the dry resin. A glass rod was immersed in the inoculum and then immersed in the dry resin for 2 seconds. The glass rod was then washed in 100 ml phosphate buffer to wash out the microorganisms. Following the standard method for evaluation of water, the collected sample was then plated and incubated. This procedure was then repeated for 5, 10 and 15 seconds.

The procedure was also repeated for the two other different humidity content batches of Resin I-A'. The results of the test are shown in table 11a.

TABLE 11a

| | number of viable microorganisms per time period | | | |
|---|---|---|---|---|
| % humidity | 2 sec. | 5 sec. | 10 sec. | 15 sec. |
| 110% | 16 | 0 | 0 | 0 |
| 50% | 23 | 1 | 0 | 0 |
| 0% | 67 | 15 | 0 | 0 |

As may be seen from table 11a, the Resin I-A' whether wet, humid or dry destroys large quantities of resistant bacteria in direct contact, and this destruction occurs on a relatively rapid time base as demonstrated above.

EXAMPLE 11.2

*Klebsiella Terrigena* Eradication Study: Air Flow

A study was done to evaluate the biocidal effectiveness of dry Resin I-A' versus *Klebsiella Terrigena.*

The system used was the system illustrated in FIG. 5. The system included an atomizer 7 (of known construction) disposed in a housing 8 provided with an air opening 9. The system had a vacuum pump 11 for the displacement of air through the system. The system included an air sterilizer 12 comprising a hollow housing 10 inches high by about 2.5 inches in inner diameter and filled with about 1.5 kilograms of Resin I-A'; the sterilizer has an air inlet and outlet. The air path through the cartridge 1 is designated by the arrows 14. The atomizer 7 contained an inoculum 16 (*Klebsiella Terrigena:* $10^7$×100 ml). For the test, the air flow at arrow 13 was set at 30 liters per minute and the air inflow at arrow 17 for the atomizer was set at 8 liters per minute; the atomizer 7 injected mist or spray 18 of inoculum into the air in the air path and the inoculated air then passed through cartridge 1 as shown by the arrows 14.

A cartridge 1 as illustrated in FIGS. 3 and 4 was prepared using dry Resin I-A' (65.0 gm giving a bed depth of 1.15 cm). The cartridge 1 was submitted to an injection of a total of 10 ml of inoculum over a time period of 15 minute. Sampling was done at 0 minutes, 7.5 minutes and at 15 minutes. The samples were collected in a standard impinger as shown in FIG. 5. After, processing 100 ml of the water from the impinger on microbiological paper filter and incubation, the results show total eradication of *Klebsiella Terrigena.*

EXAMPLE 11.3

*Bacillus Pumilus* Eradication: Air Contact

A study was carried out using the system shown in FIG. 6. To the extent that members of the system are the same as those used in the system illustrated in FIG. 5, the same reference numerals are used to identify the same parts. The main difference between the system of FIG. 5 and that of FIG. 6 is that the system of FIG. 6 uses a microbiological filter paper 19 to collect the microorganisms leaving the cartridge 1; the filter paper is maintained in place in any (known) suitable fashion.

An inoculum 20 of the thermophilic bacteria *Bacillus Pumilus* was prepared and injected at a concentration of $10^3$/liter of influent air. A cartridge mask containing 65.00 gm of Resin I-A' was prepared as for the previous example. The test ran for 30 minutes.

All effluent (velocity at arrow 13 being 30 liters per minute) was collected on the microbiological filter paper 19 (from millepore), then lain in a T.S.A. (trypticase Soy Agar) and incubated. the results showed total eradication of *Bacillus Pumilus.*

EXAMPLE 11.4

Bacillus SubtilisSterilization in Air Flow

This test was performed with *Bacillus Subtilis* in a mixture of 40% active bacteria/60% spores. The system shown in FIG. 6 was used with the cartridge comprising 50 grams of Resin I-A' (giving a bed depth of 0.85 cm). The controlled concentration of processed air was 55 bacteriological units per liter. The air velocity was 23 liter per minute for 80 minutes.

Once the 80 minutes ended, the millepore filter paper was collected, lain on T.S.A. (after neutralisation of potential iodine with sodium thiosulfate 5%) and incubated for 48 hours at 37 degree celsius. The results show a total eradication of micro-organisms.

EXAMPLE 11.5

*Bacillus Subtilis:* Resin I-A' Versus Glass Beads in Air Flow

In order to assess the retention factor of micro-organisms on inert materials this test was performed. Also, to evaluate the migration factor of the biological vector, a sequential incubation was performed.

Two gas cartridges were built in accordance with FIGS. 3 and 4, namely:

a) Resin I-A' cartridge:

10 micron polypropylene upstream mesh (filter);

: 50.00 gm of Resin I-A' giving a bed depth of 0.85 cm;

: 10 Micron polypropylene downstream mesh (filter).

b) glass bead cartridge:

10 micron polypropylene upstream mesh (filter);

: 50.0 gm sterile glass beads (from Fisher Scientific and having the same size as the beads of Resin I-A') giving a bed depth of 0.85 cm; and : 10 Micron polypropylene downstream mesh (filter).

The system as shown in FIG. 6 was used for the tests.

Simultaneously, the two cartridges were, once inserted in their respective testing chamber, submitted to a velocity of 23 liter per minutes for 40 minutes with a microbiological load of 40 bacteria per liter in the influent.

Once the test period completed, the two cartridges were dissected in sterile conditions and the microbiological filter paper recovered. Each materials composing the masks were individually as well as the filter paper were incubated in T.S.A. for 48 hours at 37 degree celsius. The results are shown in table 11*b*.

TABLE 11b

|  | Resin I-A' | Glass beads |
| --- | --- | --- |
| upstream mesh: | 2 cfu | tnc* cfu |
| Resin\beads: | 0 cfu | tnc* cfu |
| downstream mesh: | 0 cfu | 220 cfu |
| microbiological filter paper: | 0 cfu | 86 cfu |

*tnc = microorganisms too numerous to count

As may be seen from table 11b the Resin I-A' eradicated all bacteria and no living micro-organism can live in the resin bed.

The Glass beads on the other hand have a mechanical filtering capacity in regards to the biological vector but migration occurs rapidly thus obtaining "tnc" results (too numerous to count) on the upstream mesh and the beads themselves. The migration keeps on going through the filter until it reaches the microbiological paper filter in large number. Also, the glass beads filter becomes severely contaminated, causing a disposal problem.

EXAMPLE 11.6

*Bacillus Subtilis:* Resin Bed Depth Comparison

This test was performed to establish the biocidal effectiveness of the Resin I-A' in regards to the microbiological eradication of *Bacillus Subtilis*. The system of FIG. 6 was used.

Two cartridges as illustrated in FIGS. 3 and 4 containing respectively 30.00 gm (giving a bed depth of 0.5 cm) and 50.00 Gr (giving a bed depth of 0.85 cm) of Resin I-A were submitted to 60 minutes of air pumping at a velocity of 27 liter per minutes. A total of 23 ml of inoculum at a concentration of $10^7$ per ml were injected into the system.

A positive control yielded a concentration of 275 cfu/liter of air at the microbiological sampling site.

The results show total eradication for both cartridges.

EXAMPLE 11.7

*Bacillus Subtilis:* Longevity Study in Air Flow

A cartridge of FIG. 3 and 4 containing 30.00 gr (bed depth: 0.5 cm) of Resin I-A' was submitted to an air flow velocity of 25 liter/minute containing a concentration of *Bacillus Subtilis* of 112 cpu/liter (positive control for correlation) for a period of 3 hrs.

The test was done using the impinger technique (of FIG. 5), with 300 ml of sterile water. Once the 3 hours completed the water from the impinger was filtered on a microbiological membrane as referred in standard method for analysis of water and waste water 17 th edition, pp. 9–97 To 9–99. The growth media was trypticase soy agar. The results after incubation for 48 hours at 37.5 degree celsius was total eradication.

EXAMPLE 12

Studies of the Fixation of Iodine at Different Iodine Concentrations

Resin I-A', Resin I-B', Resin I-B" and Resin I-A" were prepared as follows:

Resin I-A' was prepared as described in example 9.

Resin I-B' was prepared following the procedures of examples 1 and 2 except that for the resin, Amberlite IR-400 (OH⁻) (from Rohm & Hass) was used.

Resin I-B" was prepared following the procedures of examples 1 and 2 (using Amberlite 401-S) except that the amount of the $I_2$/KI mixture was adjusted so as to provide a resin comprising about 30 percent iodine at the end of the procedure in example 2; the mixture obtained at the end of the procedure of example 2 was divided into two equal parts and one part was subjected to a wash to provide the iodinated resin obtained as at the end of the procedure in example 2; and Resin I-A" was prepared by taking the remaining one half part of the intermediate mixture obtained in the preparation of Resin I-B" (mentioned above) and subjecting the mixture to the procedure of example 3 except that the elevated temperature and pressure conditions were set at 121° C. and 15 psig respectively.

The iodine content of the above iodinated resins was determined in accordance with the procedure outlined in example 5.3. The resins were also subjected to an iodine bleed test as outlined in example 7. The results are shown in table 12 below:

TABLE 12

| Resin type | Iodine % | Iodine leach |
| --- | --- | --- |
| Resin I-B' | 43.5 | 0.15 ppm |
| Resin I-A' | 41.8 | 0.05 ppm |
| Resin I-B" | 30.5 | 0.3 ppm |
| Resin I-A" | 29.0 | 0.05 ppm |

As may be seen from table 12, subjecting the resin to a high temperature/pressure treatment results in the iodine being more tenaciously fixed to the resin at different iodine concentrations.

EXAMPLE 13

Air Study with I-B"

The procedure of example 11.6 was followed using 30 grams of Resin I-B" and *Bacillus Subtilis* at a concentration of 275000 cfu per cubic meter. It was found that the Resin I-B" eradicated only 7 to 10% of the microorganisms. The results of the test show that the Resin I-B" is not as effective at eradicating microorganisms from air as is the Resin I-A'; it would be necessary to have substantially more of Resin I-B" in order to totally sterilize air as compared with the Resin I-A'.

EXAMPLE 14

Studies of the Fixation of Iodine at Different Temperatures as well as at Atmospheric and Elevated Pressures Resin 1A, Resin 2B, Resin 3A and Resin 4B were prepared as follows:

The starting resin was Amberlite 402 (OH⁻) from Rohm & Hass. 1000 grams of this resin was pretreated following the procedure outlined in example 1(i). The obtained washed resin was divided into four 200 gram portions. An iodine sludge (four portions, one for each of the above mentioned 200 gm portions of resin) was prepared as outlined in example 1(ii) but using twice the amount of materials such as the iodine and the potassium iodide. The 200 gm resin portions were each iodinated using a respective iodine sludge as follows:

Resin 1A was prepared, using an above mentioned 200 gm resin portion and a respective iodine sludge, following the procedures of examples 2 to 4 except that for the procedure of example 3 the elevated temperature and pressure conditions were set at 121° C. and 15 psig respectively (while the reaction time at the elevated conditions remained at 15 minutes);

Resin 2B was prepared, using an above mentioned 200 gm resin portion and a respective iodine sludge, following the procedure of example 2 except that the temperature of the shaking bath was maintained at 40° C.;

Resin 3A was prepared, using an above mentioned 200 gm resin portion and a respective iodine sludge, following the procedures of examples 2 to 4 except that for the procedure of example 3 the elevated temperature and pressure conditions were set at 121° C. and 15 psig respectively while the reaction time at these elevated conditions was set at 1.5 hours rather than at 15 minutes; and Resin 4B was prepared, using an above mentioned 200 gm resin portion and a respective iodine sludge, following the procedure of example 2 except that the reaction mixture was placed into a container having a loose fitting cover; the container containing the reaction mixture was placed into a heated water bath; the temperature of the reaction mixture was brought up to a boiling temperature of 100° C. to 105° C. over a period of 20 minutes and was maintained at the boiling temperature 100° C. to 105° C. for a period of 15 minutes; and thereafter the mixture was allowed to cool to room temperature over a period of about 1 hour (the reactor was not a pressure sealed reactor but one wherein the loose fitting cover allowed gas\vapour to escape such that the reaction was carried out (essentially) at atmospheric pressure—extra safety precautions had to be taken due to the violent sputtering of the reaction mixture and to the toxicity of the released gas\vapour).

The density of each of the obtained iodinated resins was determined in accordance with the procedure outlined in example 5.1. The iodine content of the above iodinated resins was determined in accordance with the procedure outlined in example 5.3. The resins were also subjected to an iodine bleed test as outlined in example 7. The results are shown in table 14 below:

TABLE 14

| Resin type | Iodine % | Iodine leach | Density |
|---|---|---|---|
| Resin 1A | 46.4 | 0.5 ppm | 1.616 gm\ml |
| Resin 2B | 48.1 | 1.5 ppm | 1.694 gm\ml |
| Resin 3A | 45.0 | 0.5 ppm | 1.661 gm\ml |
| Resin 4B | 45.7 | 1.0 ppm | 1.595 gm\ml |

As may be seen from table 14, subjecting the starting iodine\resin mixture to a treatment at essentially atmospheric pressure and a temperature of 100° C. to 105° C. or lower (resin 2B and 4B) does not result in the iodine being as tenaciously fixed to the resin as when using both a temperature above 100° C. and a pressure above atmospheric pressure (resins 1A and 3A).

EXAMPLE 15

Sterilisation Barrier Combinations for use as Wound (Sterilisation) Dressings

EXAMPLE 15.1

Preparation of Sterilisation Foam Dressing

The following starting materials were used to prepare a sterilisation foam dressing:

a particulate iodinated resin prepared in accordance with example 9 above; the resin comprising particles or beads of about 0.3 mm to about 0.7 mm;

R/O water; and as foam precursor, HYPOL foamable hydrophilic polyurethane polymer, (code: # FHP2002) from W. R. Grace & Co., Organic Chemicals Division, Lexington, Mass. 02173.

The sterilisation foam barrier was prepared as follows:

150 ml of R/O water was placed into a 300 ml beaker. The water was heated to 50° C. 10 cc of the HYPOL and 10 gm of the iodinated resin were simultaneously admixed with the heated water; mixing was accomplished with a magnetic stirring rod and was carried out before and after the addition of the HYPOL and the resin for the purpose of dispersing the resin particles as homogeneously as possible throughout the mixture. The obtained foam was set or cured in about 7 minutes; the resin particles were dispersed throughout the matrix of the foam which was of porous cellular structure (i.e. sponge like). Once set the obtained flexible foam had a semi-sphere like form (see for example FIG. 9); slices of this foam material were taken so as to provide a foam dressing having an essentially flat face for being applied against a wound. The obtained sterilisation foam was flexible and sponge like in that it could absorb liquids such as water, pus and the like.

EXAMPLE 15.2

Preparation of a Band-aid Like Sterilisation Dressing

The following starting materials were used to prepare a band-aid sterilisation dressing:

a particulate iodinated resin prepared in accordance with example 4 above; the resin comprising particles or beads of about 0.3 mm to about 0.7 mm; and a strip of polymeric material having an adhesive on one face thereof (the strip was Compeed).

The sterilisation strip barrier was prepared as follows:

An open ended ring funnel was disposed over a central area of the strip on the adhesive face thereof. Resin beads were placed in the stem of the ring funnel so as to essentialy cover the central portion of the adhesive face defined by the ring; a plunger was shoved into the ring and a mild pressure was applied to the resin beads therein. The ring was removed along with excess resin beads so as to leave behind a single layer of resin beads fixed to the adhesive face of the strip; the resin beads in the layer essentialy abutted each other. The strip barrier had a form as shown in FIG. 8; if desired the beads do not have to abut but could be spaced apart.

EXAMPLE 15.3

Animal Infection Study: Cuts

The foam type sterilisation dressing obtained from example 15.1 was tested as follows:

Eight male guinea pigs were shaved so as to expose essentially the same skin area. The guinea pigs each weighed about 500 to 550 gm and were obtained from Charles River, Quebec, Canada, a sub-division of Bausch & Lomb; the guinea pigs were quarantined for a period of 48 hours before being prepared for and subjected to the tests.

The guinea pigs were prepared for the tests as follows: Essentially the same area of skin of each of the guinea pigs was anesthetised using Carbocaine-V (chlorhydrate of Mepivacaine USP 2%); this anesthetic has no known sterilisation qualities. An inoculum comprising a mixture of *Staphillococus Aureus* and *Pseudomonas Aeriginosa* was prepared at $10^9$ cfu/ml; the ratio of *Staphillococus Aureus* to *Pseudomonas Aeriginosa* was 1:1. 0.2 ml of the inoculum was injected under the anesthetised skin of each animal. A cruciform structured scalpel cut (#) was made above the inoculum injection area of each of the animals; i.e. the cuts were 1.0 to 4.0 cm long and 1.0 to 4.0 mm deep. Additional inoculum was dabbed onto the surface cuts.

The animals were divided into two groups of four animals each, one group to be used as a control group and the other group as a test group. A foam sterilisation dressing was applied over the wound for each of the animals of the test group, i.e. the foam dressing was placed in contact with the wounded skin area and maintained in place during the period of the test. The foam dressings were maintained in place over the wound area by means of an adhesive strip which was provided with an opening or window by means of which a portion of the foam dressing was left uncovered and exposed to the air. No dressing or sterilisation material was applied to the wounds of the animals of the control group.

The four animals of the test group with dressings developed no infection and the scaring process was initiated after 16 hours. On the other hand the four control animals developed infection and the infection was still spreading after 72 hours.

The strip type sterilisation dressing obtained from example 15.2 was tested exactly as above for the foam dressing with exactly the same results.

EXAMPLE 15.4

Animal Infection Study: Burns

The same studies as described in example 15.3 were carried out except that the lesion was a burn created with a 1.0 cm red hot rod; the hot rod was firmly held against the skin for about 3 to 4 seconds. The same Inoculum as in example 15.3 was injected beneath the burn area and also dabbed onto the surface of the burned skin. Exactly the same results were obtained for the two types of dressings as were obtained for the tests of example 15.3.

EXAMPLE 15.5

Animal Infection Study: Cuts with Continual Contact with Infectious Liquid

The foam type sterilisation dressing obtained from example 15.1 was tested as follows:

Four male guinea pigs were shaved so as to expose essentially the same skin area. The guinea pigs each weighed about 500 to 550 gm and were obtained from Charles River, Quebec, Canada; the guinea pigs were quarantined for a period of 48 hours before being prepared for and subjected to the tests.

The guinea pigs were prepared for the tests as follows: Essentially the same area of skin of each of the guinea pigs was anesthetised using Carbocaine-V (chlorhydrate of Mepivacaine USP 2%); the area was also sterilised using 70% isopropyl alcohol. A cruciform structured scalpel cut (#) was then made in the sterilised area; i.e. the cuts were 1.0 to 4.0 cm long and 1.0 to 4.0 mm deep.

The animals were divided into two groups of two animals each, one group to be used as a control group and the other group as a test group. A foam sterilisation dressing was applied over the wound for each of the animals of the test group, i.e. the foam dressing was placed in contact with the wounded skin area and maintained in place during the period of the test. The foam dressings were maintained in place over the wound area by means of an adhesive strip which was provided with an opening or window by means of which a portion of the foam dressing was left uncovered and exposed. No dressing or sterilisation material was applied to the wounds of the animals of the control group.

An inoculum comprising a mixture of *Staphillococus Aureus* and *Pseudomonas Aeriginosa* was prepared at $10^7$ cfu/100 ml; the ratio of *Staphillococus Aureus* to *Pseudomonas Aeriginosa* was 1:1. Sufficient inoculum was prepared such that each of the animals of the test and control group could be bathed in the inoculum such that the bath liquid was in continual contact with the wound area, i.e. the bath liquid covered the dressings. The animals of each group were kept in the bath inoculum for a period of 72 hours.

The two animals of the test group with dressings developed no infection and the scaring process was in full process. On the other hand the two control animals each had developed infection.

EXAMPLE 15.6

Animal Infection Study: Cuts Contacted with Aerosol Borne Infectious Agents

The same procedure as for example 15.5 was used except that instead of being maintained in a bath of inoculum, the inoculum was applied using an atomiser the same as that used for example 11.2 for artificial creation of airborne infection of a wound; the inoculum used also had $10^9$ cfu/ml rather than $10^7$ cfu/100 ml as in example 15.6. 4 ml of the inoculum was sprayed directly on the wound of the control animals and on the dressing covering the wound of the test animals; the inoculum was so applied every hour for 8 hours with 72 hours of incubation. The same results as in example 15.5 were obtained.

EXAMPLE 15.7

Skin Reaction Study: Iodine Tincture

Three male guinea pigs were shaved so as to expose essentially the same skin area. The guinea pigs each weighed about 500 to 550 gm and were obtained from Charles River, Quebec, Canada; the guinea pigs were quarantined for a period of 48 hours before being prepared for and subjected to the tests.

The guinea pigs were prepared for the tests as follows: Essentially the same area of skin of each of the guinea pigs was anesthetised using Carbocaine-V (chlorhydrate of Mepivacaine USP 2%); the area was also sterilised using &0& isopropyl alcohol. A cruciform structured scalpel cut (#) was made in the sterilised area; i.e. the cuts were 1.0 to 4.0 cm long and 1.0 to 4.0 mm deep.

An inoculum comprising a mixture of *Staphillococus Aureus* and *Pseudomonas Aeriginosa* was prepared at $10^9$ cfu/ml; the ratio of *Staphillococus Aureus* to *Pseudomonas Aeriginosa* was 1:1.

The inoculum was only dabbed onto the surface of the wounds of each of the animals (no injection of inoculum under the skin). It was found that a 5% iodine tincture locally applied on the wounds would neutralise infection provided that the iodine tincture was applied at 0.1 ml directly after infection and every 2 hours thereafter for 10 hours; the iodine tincture was from Jean Coutu, Quebec, Canada—5% iodine, 3.3% KI and 75% ethanol. However, it was noted that the skin in the periphery of the wound was seriously devitalised because of the burning effect of the tincture i.e. of the iodine.

It was also found that the iodine tincture did not stop infection from occurring if inoculum was injected under the skin.

EXAMPLE 15.8

Skin Reaction Study: Sterilisation Dressings

Three male guinea pigs were shaved so as to expose essentially the same skin area. The guinea pigs each weighed about 500 to 550 gm and were obtained from Charles River, Quebec, Canada; the guinea pigs were quarantined for a period of 48 hours before being subjected to the tests.

A foam sterilisation dressing of example 15.1 was applied over a shave skin area of each of the animals, i.e. the foam dressing was placed in contact with the shaved skin area and maintained in place during the period of the test. The foam dressings were maintained in place over the skin area by means of an adhesive strip which was provided with an opening or window by means of which a portion of the foam dressing was left uncovered and exposed to the air. The dressing was maintained in place for a period of 3 weeks. The covered skin area was examined every two days. No redness, rash, inflammation, or any other reaction was noted; the covered skin remained healthy.

The above procedure was also carried out using a strip sterilisation dressing of example 15.2. However the dressing was maintained in place only for 7 days. Again, no redness, rash, inflammation, or any other reaction was noted; the covered skin remained healthy.

FIGS. 7 to 11 illustrate a number of example embodiements of sterilisation barrier combinations of the present invention; some of these combinations are also described in example 15 above.

FIG. 7 shows a partially cut away perspective view of a sterilisation barrier dressing of tea-bag type construction wherein the iodinated resin particles or beads (one of which is designated by the reference numeral 30) are free flowing but are held together by being enveloped by a fluid (e.g. air-liquid) permeable envelope 31 of (known) pharmaceutically acceptable paper or gauze (e.g. a suitable sterile gauze from Johnson & Johnson, Canada). The paper or gauze is permeable to fluids such as air and water but is able to hold onto the particles of iodinated resin enveloped thereby since any holes in the paper gauze are sized to be smaller than the particles of resin. This type of dressing may be made relatively small or relatively large keeping in mind the size of the lesion that it is intended to cover. The dressing may be made by providing a sheet of paper or gauze, placing the desired amount of resin particles thereon and then folding one side edge of the paper or gauze over the resin particles 30 so as to overlay and abut the opposite side; these abuting side edges 32 and 33 as well as each of the respective side edges of the two pairs of adjacent side edges indicated generally at 34 and 35 may be fixed together in any known manner, for example by compression, stitching or by the use of any known phamaceutically acceptable adhesive. The fixation of the sides is such that they will tend to maintain their integrity in the face of water, body fluids or body exudates (e.g. pus). The embodiment shown in FIG. 7 is shown may be considered as essentially having a plurality of resin bead layers; it could of course have only a single such layer.

Alternatively, the sterilisation barrier may take on a band-aid type aspect as shown in FIG. 8. The combination shown has a flexible carrier component 36. A central portion of one side of the carrier component 36 has fixed thereto a plurality of beads or particles (one of which is designated by the reference numeral 37) of demand disinfectant iodinated resin. The resin beads 37 are fixed to the surface by a suitable adhesive which is pharmaceticatly acceptable and which will maintain the beads on the carrier component even if exposed to water or body fluids or exudates. The portion of the band surface 38 which surrounds the centrally disposed beads 36 may also be provided with any (known) adhesive which may for example be able to releasably stick the combination to the skin (e.g. a latex based adhesive). The carrier component 36 may, as desired be permeable or impermeable to fluids such as air, water, pus; prefereably, the carrier is permeable to gas such as air, water vapour, etc. at least in the region of the resin beads fixed thereto, i.e. this region is air breathable. The carrier component 36 may be of any suitable pharmaceutically acceptable (plastics) material (e.g. the carrier component may be a porous hydrophobic material permeable to air and water vapour such as described in U.S. Pat. Nos. 3,953,566 and 4,194,041—Gore-Tex). The carrier component complete with an adhesive face may be obtained from Peco Marketing ltd., Montreal, Quebec under the name "Compeed".

FIGS. 9, 10 and 11 show a number of further embodiments of the sterilisation barrier combination.

FIG. 9 shows a flexible sterilisation foam or sponge type dressing 39 for wounds. The dressing comprises a flexible pharmaceutically acceptable foam matrix 40 having iodinated resin particles (one of which is designated with the reference numeral 41) dispersed therein. The foam matrix 40 has a porous open cell structure such that it is permeable to fluids such as air and water and can absorb body liquids in the manner of a sponge (e.g. the foam is hydrophilic and/or oil loving); the foam barrier is air breathable. The foam matrix 40 as shown has cells of relatively small size so as to facilitate the absorption of liquids such as pus. The resin particles 41 making up the resin disinfectant component are distributed throughout and held or fixed in place by the polymeric matrix 40 such that surface portions of the resin particles are exposed within the cells of the matrix 40. The exposed surfaces of the resin are available for contact with any microorganisms which may find their way into the cells of the body of the barrier combination; contact with the resin devitalises the microorganisms.

The foam sterilisation barrier or dressing 39 as shown in FIG. 9 has a semi-spherical like shape. The flat surface 42 may be applied to a wound or cut. The dressing may be held in place by any suitable means such as for example any suitable strapping or by adhesive tape means. Preferably, the sterilisation foam dressing 39 is held in place such that at least a portion of it is exposed (e.g. exposed to the air); thus the means for holding the foam in place may be an adhesive strip which has a central opening exposing at least a portion of the foam when the foam is held in place. Once in place on the wound, the flexible foam sterilisation barrier will sterilise the immediate area of the wound which it covers and also prevent other infectious microorganisms from contacting the wound from outside the body. Surprisingly, however, it has been found that the sterilisation barrier is also effective not only against microorganisms at the immediate surface of a wound but also against those deeper within the body in the area of a cut.

FIG. 10 illustrates another type of flexible foam sterilisation barrier 43. It differs from the sterilisation barrier shown in FIG. 9 in that the size of the cells (one of which is designated with the reference numeral 44) is significantly larger than those for the foam shown in FIG. 9; this type of foam may be used as a liner material for wearing apparel to provide the apparel with the ability to protect the wearer from (skin) contact with viable microorganisms. The resin beads, spheres or particles (one of which is designated with the reference numeral 45) are, as in the case of the resin spheres 41 for the foam barrier 39 of FIG. 9, dispersed in the foam matrix and are held or fixed in place thereby such that exposed surfaces of the resin are available for contact with any microorganisms which may find their way into the cells of the body of the barrier combination; contact with the resin devitalises the microorganisms.

The foam matrix for the sterilisation barriers of FIGS. 9 and 10 may be made by admixing (known) starting reactants in (known) manner to make (known) foams which are pharmaceutically acceptable. Known polyurethane foams may for example be used. In order to make the sterilisation barrier, the disinfectant resin particles may be admixed with and dispersed (e.g. more or less homogeneously) in the starting reactants at the beginning of the foam producing reaction. The foam barrier may be set in molds or else cut to the desired shape. The foam sterilisation barrier may take any desired form such as sheets, films, plugs, and the like; it may, for example, be molded so as to conform to the shape of portion of the body to which it is to be applied.

As mentioned above a (flexible) phamaceutically acceptable hydrophilic foam matrix may be obtained using water and HYPOL foamable hydrophilic polyurethane polymer starting material from W. R. Grace & Co. Lexintington Mass. U.S.A.

The pore or cell size of the foam barrier may be adjusted in known manner; for example by altering the reaction temperature. For example in the case of HYPOL a temperature of about 50 to 70° C. may be used to obtain small pore sizes and a lower temperature of about 35 to 45° C. may be used to obtainer larger sized pores.

FIG. 11 shows a cross sectional portion of a sandwich type textile material 46 which incorporates a flexible large cell size sterilisation foam layer 47. The sandwich comprises two outer flexible clothe type layers 48 and 49 which are fixed to the central sterilisation foam barrier 46 in any suitable manner (e.g. by an adhesive, melt fusion, etc.). The two outer layers 48 and 49 may be of any desired material; they may be permeable or impermeable to fluids such as air, water vapour, water and the like. They may for example be of cotton, polypropylene, etc.; or a Gore-tex type material mentioned above. A sheet of textile material as shown may cut into pieces of various shapes needed to form such protective wearing apparel as may be desired, e.g. coats, pants, socks, face masks (e.g. full face masks or masks covering only the mouth and nose) and the like.

The flexible foam layer 47 can be made in any known manner provided that disinfectant resin particles are dispersed in the reaction mixture during the reaction such that the end product foam also has the resin particles dispersed in the foam matrix and any microorganism able to penetrate into an interior cell of the foam may be able to contact a resin particle exposed into the cell and be devitalised thereby. The foam barrier as in the case of the foam dressings mentioned may be configured to be permeable to fluids such as air, water, etc.

The textile material 46 may be formed by first forming a sheet of the sterilisation foam; by providing sheets of the desired outer layers; and then gluing the elements together such that the foam is sandwiched between the two other outer layers. Alternatively, a mold may be used wherein opposed surfaces of the mold are provided with a respective outer layer; the foam starting materials are introduced between the layers; and foaming activated such that the foam layer is produced in situ.

Although shown with two outer layers the combination of FIG. 11 may of course have only one such clothe like layer. Additionally if the outer layer or layers are permeable to fluids such as air, water, pus and the like, the wearing apparel made therefrom could as needed double as a kind of sterilisation dressing; the textile may thus for example be air breathable.

Additionally although the foam sterilisation barrier has been described in relation to a flexible foam it may be a stiff foam depending upon the application; again the stiff foam matrix may be prepared in known manner.

An alternate embodiement of the sandwich type textile may be made wherein the foam matrix is omitted; in this case the beads may be placed between the outer layers and the beads may be fixed in place for example by an adhesive or by melt fusion depending on the nature of the layers (e.g. melt fusion may be considered if the layers are of thermoplastics material; the textile may of course be so made as to preserve the flexibility of the combination.

I claim:

1. A sterilisation dressing, for being applied to a lesion, said dressing comprising
   a demand disinfectant component
   and a carrier component,
said demand disinfectant component comprising of an iodinated anion exchange resin, said demand disinfectant component being held to said carrier component such that microorganisms are able to be brought into contact with said particles and be devitalized thereby, said carrier component is a polymer.

2. A dressing as defined in claim 1 wherein said carrier component is flexible and has an outer surface and wherein particles of said demand disinfectant are fixed to at least a portion of said outer surface.

3. A dressing as defined in claim 1 wherein said carrier component is flexible and comprises a porous cellular polymeric matrix, wherein said demand disinfectant is dispersed in said polymeric matrix.

4. A dressing as defined in claim 1 wherein said iodinated anion exchange resin comprises an anion exchange resin component which represents from 25 to 90 percent by weight of the total weight of the iodinated resin.

5. A dressing as defined in claim 1 wherein said iodinated anion exchange resin comprises an anion exchange resin component which represents from 45 to 65 percent by weight of the total weight of the iodinated resin.

6. A dressing as defined in claim 1 wherein said iodinated strong base anion exchange resin is an iodinated anion exchange resin prepared in accordance with a process comprising a conversion step, the conversion step comprising contacting a porous anion exchange resin in a salt form with a sufficeint amount of an iodine-substance absorbable by the anion exchange resin such that the anion exchange resin absorbs said iodine-substance so as to convert the anion exchange resin to the demand disinfectant resin, said iodine-substance being selected from the group consisting of $I_2$ and polyiodide ions having a valence of −1, characterized in that for the conversion step of at least a portion of the absorbtion of iodine-substance is effected at elevated temperature and at elevated pressure, said elevated temperature being higher that 100° C., said elevated pressure being greater than atmospheric pressure.

7. A dressing as defined in claim 1 wherein said iodinated anion exchange resin is an iodinated anion exchange resin prepared in accordance with a process comprising a conversion step, the conversion step comprising contacting a porous anion exchange resin in a salt form other than the iodide form I−, with a sufficient amount of an iodine-substance absorbable by the anion exchange resin such that the anion exchange resin absorbs said iodine substance so as to convert the anion exchange resin to the demand disinfectant resin, said iodine being selected from the group consisting of polyiodide ions having a valence of −1, characterized in that said conversion step comprises an initial conversion stage followed by a second conversion stage, in that said initial conversion stage comprises contacting the anion exchange resin with the iodine-substance at a temperature of 100° C. or lower so as to obtain an intermediate composition, said intermediate composition comprising residual absorbable iodine-substance and an intermediate iodinated resin, and in that said second conversion stage comprises subjecting the intermediate composition to elevated temperature and elevated pressure, said elevated temperature is a temperature of 102° C. or higher, said elevated pressure is a pressure of from 2 psig to 35 psig and wherein said iodine-substance comprises triiodide ions of formula $I_3$, and wherein said anion exchange resin is in the hydroxyl from OH−; wherein the anion exchange resin is contacted with a composition consisting of a mixture of KI, $I_2$ and a minor amount of water, the mole ratio of KI to $I_2$ initially being about 1.

8. A dressing as defined in claim 3 wherein said iodinated anion exchange resin is a iodinated anion exchange resin prepared in accordance with a process comprising a conversion step, the conversion step comprising contacting a porous anion exchange resin in a salt form other than the iodide form I−, with a sufficient amount of an iodine-substance absorbable by the anion exchange resin such that the anion exchange resin absorbs said iodine substance so as to convert the anion exchange resin to the demand disinfectant resin, said iodine-substance being selected from the group consisting of polyiodide ions having a valence of −1, characterized in that said conversion step comprises an initial conversion stage followed by a second conversion stage, in that said initial conversion stage comprises contacting the anion exchange resin with the iodine-substance at a temperature of 100° C. or lower so as to obtain an intermediate composition, said intermediate composition comprising residual absorbable iodine-substance and an intermediate iodinated resin, and in that said second conversion stage comprises subjecting the intermediate composition to elevated temperature and elevated pressure, said elevated temperature is a temperature of 102° C. or higher, said elevated pressure is a pressure of from 2 psig to 35 psig and wherein said iodine-substance comprises triiodide ions of formula $I_3^-$, and wherein said anion exchange resin is in the hydroxyl form OH−, wherein the anion exchange resin is contacted with a composition consisting of a mixture of KI, $I_2$ and a minor amount of water, the mole ratio of KI to $I_2$ initially being about 1.

9. A sterilization dressing, for being applied to a lesion, said dressing comprising a disinfectant component and a carrier component, said disinfectant component comprising an iodinated resin, said carrier component being configured so as to bold onto said disinfectant component such that microorganisms are able to be brought into contact with said particles and be devitalised thereby, said carrier component is a polymer.

10. A method for disinfecting a body fluid containing microorganisms, said method comprising contacting said body fluid with a demand disinfectant resin such that microorganisms therein contact said resin and are deactivated thereby, said disinfectant resin being an iodinated strong base anion exchange resin.

11. A method for disinfecting a body fluid as defined in claim 10 wherein said iodinated strong base anion exchange resin comprises a strong base anion exchange resin component which represents from 25 to 90 percent by weight of the total weight of the iodinated resin.

12. A method for disinfecting a body fluid as defined in claim 10 wherein said iodinated strong base anion exchange resin comprises a strong base anion exchange resin component which represents from 45 to 65 percent by weight of the total weight of the iodinated resin.

* * * * *